(12) United States Patent
Zaidi et al.

(10) Patent No.: US 8,435,948 B2
(45) Date of Patent: May 7, 2013

(54) METHODS FOR INHIBITING OSTEOCLASTIC BONE RESORPTION AND BONE LOSS COMPRISING ADMINISTRATION OF AN ANTI-FSH OR ANTI-FSHR ANTIBODY

(75) Inventors: Mone Zaidi, Riverdale, NY (US); Harry C. Blair, Pittsburgh, PA (US)

(73) Assignees: Mount Sinai School of Medicine of New York University, New York, NY (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 479 days.

(21) Appl. No.: 11/664,030

(22) PCT Filed: Sep. 27, 2005

(86) PCT No.: PCT/US2005/035019
§ 371 (c)(1),
(2), (4) Date: Nov. 30, 2007

(87) PCT Pub. No.: WO2006/039400
PCT Pub. Date: Apr. 13, 2006

(65) Prior Publication Data
US 2008/0069811 A1    Mar. 20, 2008

Related U.S. Application Data

(60) Provisional application No. 60/620,086, filed on Oct. 18, 2004, provisional application No. 60/614,597, filed on Sep. 29, 2004.

(51) Int. Cl.
*A61K 39/00*     (2006.01)
*A61K 39/395*    (2006.01)
*A61K 38/00*     (2006.01)

(52) U.S. Cl.
USPC ...  514/16.7; 514/16.9; 424/130.1; 424/141.1; 424/142.1; 424/145.1; 424/143.1

(58) Field of Classification Search .................. None
See application file for complete search history.

(56) References Cited

U.S. PATENT DOCUMENTS

| 5,639,640 | A  | 6/1997 | Reddy et al. |
| 2002/0042149 | A1 | 4/2002 | Butlin et al. |
| 2002/0058654 | A1 | 5/2002 | Coats et al. |
| 2003/0144203 | A1 | 7/2003 | Bowen |

FOREIGN PATENT DOCUMENTS

WO    WO 03/053219    *  7/2003

OTHER PUBLICATIONS

Jerilynn Prior, Trends in Molecular Medicine, 2006; 13: 1-3.*
Zaidi et al., Cell, 2006; 127: 1080-81.*
Robinison et al., Biochem Biophys Res Commun. 2010; doi10.1016/j.bbrc.2010.02.112; Article in Press: 6 pages total.*
Maillefert et al. British Journal of Rheumatology, 1994; 33: 1199-1200.*
Reindollar et al., Fertility and Sterility, 2002; 78: 469-472.*
Phillips, A., J Pharm Pharmacology 53: 1169-1174, 2001.*
Vidal et al., European Journal of Cancer. 41: 2812-2818, 2005.*
Pirollo et al. Cancer Res. 68(5): 1247-1250, 2008.*
Allan et al., PNAS, 2010; 107: 22629-22634.*
Iqbal et al. (2006) *Proc. Natl. Acad. Sci* 103:14925-14930.
Kraus et al (2001) *Archives of Medical Research* 32:499-509.
Martin et al. (2006) *Nature Medicine* 12:612-613.
Zijlstra-Westhoff et al. (1998) *Journal of Reproductive Immunology* 38:139-154.

* cited by examiner

*Primary Examiner* — Bridget E Bunner
*Assistant Examiner* — Christina Borgeest
(74) *Attorney, Agent, or Firm* — Fox Rothschild LLP

(57) ABSTRACT

The invention discloses compositions and methods for decreasing osteoclast which are useful for the treatment of a variety of bone loss disorders.

10 Claims, 18 Drawing Sheets

GCTCCCAGAGTCACCAATAGTTACGTGCTTGTCCCTCTAAATCAT
TCAGTCCAGAACTAAAAATCAATGTGAAAATGGATCCTCACCTTG
AAAGACAAGTGTGACTTCTTTCTGGAGAGAGGGCTATGGAAGAGC
TGGCAGTGTTGCTACATATTTCATCTAATTTAATCTTTCTAGGTA
TGTGCATGGCAGATAGGTCAGGG (SEQ ID NO: 1)

Immunolabeling Osteoclast FSH Receptors

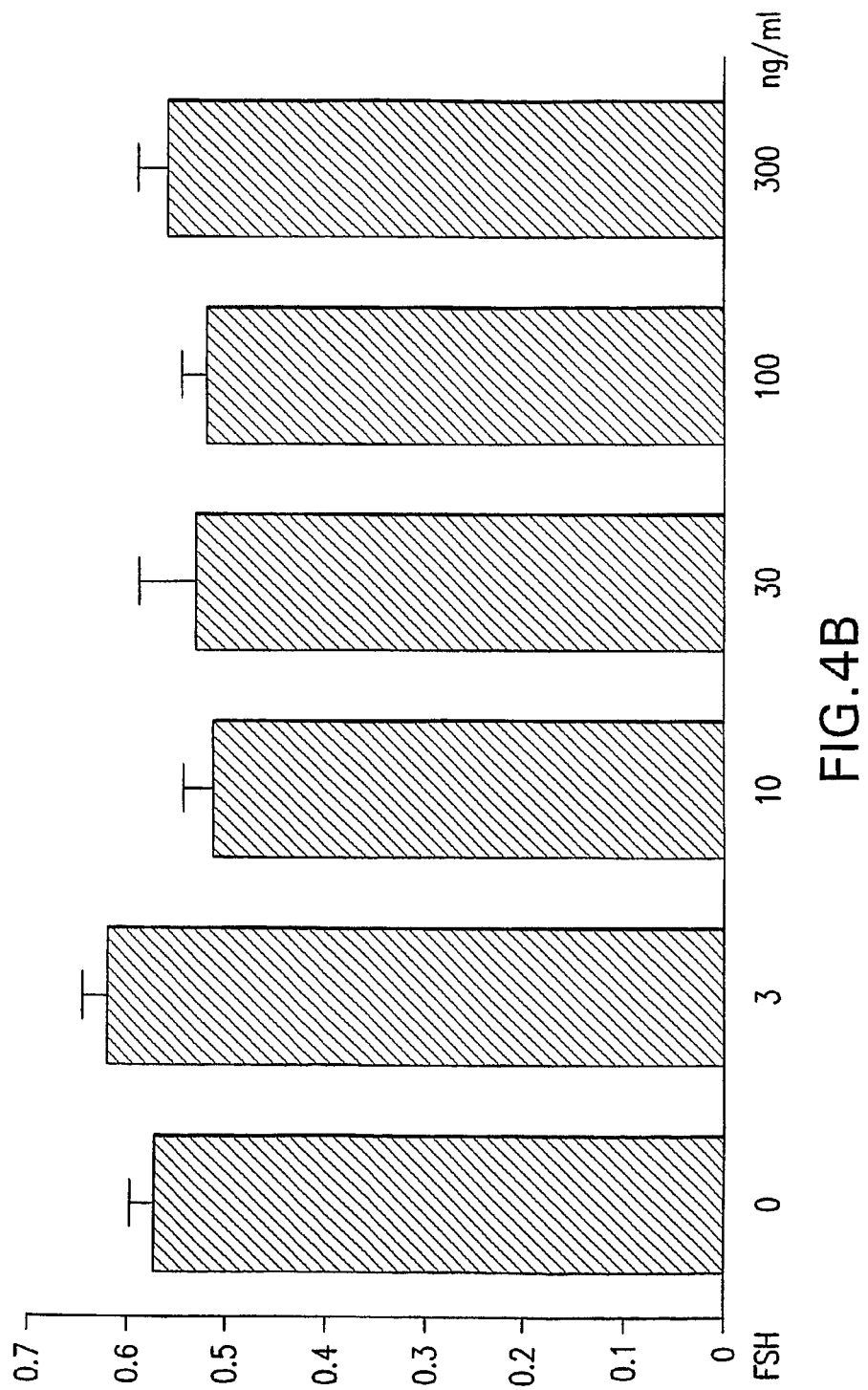

NO FSH    50 ng/ml FSH

At 7 d in RANKL (20ng/ml) and CSF-1 (10 ng/ml) osteoclast differentiation is minimal in control cells but TRAP and multinucleation are seen with FSH

SEQUENCE LISTING

```
<160> NUMBER OF SEQ ID NOS: 1

<210> SEQ ID NO 1
<211> LENGTH: 204
<212> TYPE: DNA
<213> ORGANISM: Mus musculus

<400> SEQUENCE: 1
gctcccagag tcaccaatag ttacgtgctt gtccctctaa atcattcagt ccagaactaa      60
aaatcaatgt gaaaatggat cctcaccttg aaagacaagt gtgacttctt tctggagaga     120
gggctatgga agagctggca gtgttgctac atatttcatc taatttaatc tttctaggta     180
tgtgcatggc agataaggtc aggg                                            204
```

METHODS FOR INHIBITING OSTEOCLASTIC BONE RESORPTION AND BONE LOSS COMPRISING ADMINISTRATION OF AN ANTI-FSH OR ANTI-FSHR ANTIBODY

CROSS-REFERENCE TO RELATED APPLICATION

This application claims the benefit of U.S. Application Ser. No. 60/614,597 filed Sep. 29, 2004 and U.S. Application Ser. No. 60/620,086 filed Oct. 18, 2004, the disclosures of which are incorporated herein by reference.

GOVERNMENT SUPPORT

This invention was made with government support under grant number AG14917-08 awarded by the National Institute on Aging of the NIH. The government has certain rights in the invention.

FIELD OF THE INVENTION

The invention concerns the physiological processes of bone deposition and bone resorption. The invention relates to osteoclast development, survival and function and compositions and methods that prevent osteoclast development, survival and function, and hence prevent bone loss.

BACKGROUND

Osteoporosis is a crippling bone disease that poses a major public health problem. Around 44 million Americans, both men and women, suffer from the disease. It is silent and hence, most often under-diagnosed. It causes fractures, most notably hip, spinal and wrist fractures that result in disability and death.

Osteoporosis in women after the menopause is thought to result from low estrogen levels that accompany ovarian failure. It has been shown that estrogen can directly control excessive bone removal by its action on the osteoclast, a cell unique in its ability to resorb bone. Normally, the activity of the osteoclast is tightly coupled to that of the osteoblast, a cell that forms new bone. When osteoclastic bone resorption is in excess of bone formation, more bone is lost than is gained with resulting gaps in bone, which becomes prone to fracture and collapse.

There is convincing evidence that the post-menopausal increase in bone resorption results from an absolute increase in number of osteoclasts resident in bone, rather than from the enhanced activity of individual cells. This is due to the increased recruitment of new osteoclasts from bone marrow. Replacement of estrogen corrects this defect, and it has thus been speculated that declining estrogen levels are solely responsible for the increased osteoclastogenesis and post-menopausal bone loss.

Follicle-stimulating hormone (FSH) is a glycoprotein hormone synthesized and secreted by the pituitary. It causes the synthesis and secretion of estrogen by interacting with its receptor, the FSH receptor, on the follicular cell of the ovary. Estrogen levels, in turn, control FSH release from the pituitary through a well-known feedback mechanism. Thus, when estrogen rises, FSH falls. Likewise, when the ovaries fail during menopause, FSH levels rise. FSH has, however, never been implicated directly in causing post-menopausal bone loss, although serum FSH levels have been shown to correlate with bone remodeling increases in women (Kawai et al, 2004; Sowers et al, 2003).

Thus, estrogen depletion may not completely explain post-menopausal bone remodeling. Accordingly, there exists a need in the art for identification of additional factors that contribute to osteoporosis and other osteoclast-mediated disease characterized by bone loss.

SUMMARY

The invention provides compositions and methods for modulating osteoclast formation, survival and function. The follicle stimulating hormone receptor modulators (FHSRMs) and follicle stimulating hormone modulators (FSHMs) disclosed herein are potent modulators of osteoclast activity, and methods of using FSHRM and FSHM compositions to decrease osteoclastic bone resorption are provided. These FSHRM and FSHM compositions are useful for modulating bone remodeling, maintenance, and repair.

In one aspect, the invention provides compositions and methods for decreasing osteoclast activity in a cell population comprising at least one osteoclast or osteoclast precursor cell. The methods involve contacting the osteoclast or osteoclast precursor cell with an FSHRM composition, whereby contact with the FSHRM composition decreases osteoclast activity, survival and function.

In one aspect, the invention provides compositions and methods for decreasing osteoclast activity in a cell population comprising at least one osteoclast or osteoclast precursor cell. The methods involve providing an FSHM composition, whereby contact with the FSHM composition decreases osteoclast activity, survival and function.

In one embodiment, methods for decreasing osteoclast-mediated bone resorption are provided. The methods involve contacting osteoclasts or osteoclast precursor cells with an FSHRM composition, whereby the FSHRM composition decreases osteoclast-mediated bone resorption by decreasing the osteoclast activity of the osteoclasts already present or decreasing the differentiation of osteoclast precursor cells or preventing survival by inducing apoptosis in the osteoclast or its precursor.

In one embodiment, methods for decreasing osteoclast-mediated bone resorption are provided. The methods involve providing cells with an FSHM composition, whereby the FSHM composition decreases osteoclast-mediated bone resorption by decreasing the osteoclast activity of the osteoclasts already present or decreasing the differentiation of osteoclast precursor cells or preventing survival by inducing apoptosis in the osteoclast or its precursor.

In one aspect, the invention provides compositions and methods for the treatment of bone loss disorders. "Bone loss disorders" include conditions and diseases wherein the inhibition of bone loss is desirable. Among such conditions and diseases are osteoporosis, osteomyelitis, Paget's disease, periodontitis, hypercalcemia, osteonecrosis, osteosarcoma, osteolyic metastases, familial expansile osteolysis, prosthetic loosening, periprostetic osteolysis, cleiodocranial dysplasia (CCD), multiple myeloma, and bone loss due to arthritides. The methods involve administering an FSHRM or FSHM composition to a patient having a bone loss disorder. Also provided are methods for decreasing osteoclast activity in a patient having a bone loss disorder using an FSHRM and/or FSHM composition.

In a preferred embodiment, the invention provides methods for treating a variety of osteoporosis disorders, such as primary osteoporosis, endocrine osteoporosis (hyperthyroidism, hyperparathyroidism, Cushing's syndrome, and acromegaly), hereditary and congenital forms of osteoporosis (osteogenesis imperfecta, homocystinuria, Menkes' syndrome, and Rile-Day syndrome) and osteoporosis due to immobilization of extremities, steroid-induced osteoporosis, and immunosuppressant (post-transplant) osteoporosis. Also provided are methods for decreasing osteoclast activity in patients having an osteoporosis disorder. The methods involve administering an FSHRM and/or FSHM composition to a patient having an osteoporosis disorder.

In another preferred embodiment, the invention provides methods for treating osteomyelitis, or an infectious lesion in bone leading to bone loss. Also provided are methods for decreasing osteoclast activity in patients having osteomyelitis, or an infectious lesion in bone leading to bone loss. The methods involve administering an FSHRM and/or FSHM composition to a patient having osteomyelitis, or an infectious lesion in bone leading to bone loss.

In another preferred embodiment, the invention provides methods for treating osteosarcoma. Also provided are methods for decreasing osteoclast activity in patients having osteosarcoma. The methods involve administering an FSHRM and/or FSHM composition to a patient having osteosarcoma.

In another preferred embodiment, the invention provides methods for treating osteonecrosis, or bone cell death, associated with traumatic injury or nontraumatic necrosis associated with Gaucher's disease, sickle cell anemia, systemic lupus erythematosus and other conditions. Also provided are methods for decreasing osteoclast activity in patients having osteonecrosis. The methods involve administering an FSHRM and/or FSHM composition to a patient having osteonecrosis.

In another preferred embodiment, the invention provides methods for inhibiting bone loss attendant rheumatoid arthritis and other arthritides that cause bone loss. Also provided are methods for decreasing osteoclast activity in patients having rheumatoid arthritis. The methods involve administering an FSHRM and/or FSHM composition to a patient having rheumatoid arthritis.

In another preferred embodiment, the invention provides methods for treating periprosthetic osteolysis. Also provided are methods for decreasing osteoclast activity in patients having periprosthetic osteolysis. The methods involve administering an FSHRM composition to a patient having periprosthetic osteolysis.

In another preferred embodiment, the invention provides methods for treating bone loss due to osteolytic metastasis or humoral hypercalcemia of malignancy. Also provided are methods for decreasing osteoclast activity in patients having osteolytic metastasis or humoral hypercalcemia of malignancy. The methods involve administering an FSHRM and/or FSHM composition to a patient having osteolytic metastasis or humoral hypercalcemia of malignancy.

In another preferred embodiment, the invention provides methods for treating familial expansile osteolysis. Also provided are methods for decreasing osteoclast activity in patients having familial expansile osteolysis. The methods involve administering an FSHRM and/or FSHM composition to a patient having familial expansile osteolysis.

In another preferred embodiment, the invention provides methods for treating Paget's disease (osteitis deformans). Also provided are methods for decreasing osteoclast activity in patients having Paget's disease. The methods involve administering an FSHRM and/or FSHM composition to a patient having Paget's disease.

In another preferred embodiment, the invention provides methods for treating CCD. Also provided are methods for decreasing osteoclast activity in patients having CCD. The methods involve administering an FSHRM and/or FSHM composition to a patient having CCD.

In another preferred embodiment, the invention provides methods for decreasing prosthetic loosening. Also provided are methods for decreasing osteoclast activity in patients having a prosthesis. The methods involve administering an FSHRM and/or FSHM composition to a patient having a prosthesis.

DETAILED DESCRIPTION OF THE PREFERRED EMBODIMENTS

Figure 1:
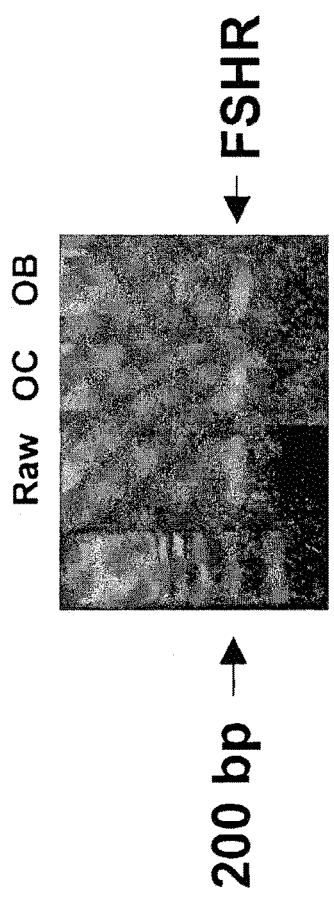
FIG. 1 shows RT-PCR evidence that FSH receptors are present on osteoclasts in primary cultures as well as in RAW264.7 cells. The sequence of the PCR product in all cases showed a 100% match with the known receptor sequence.
Figure 1:
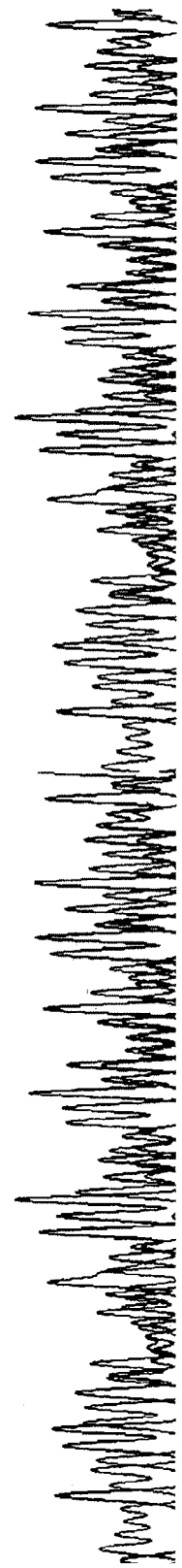

It has now been found that follicle stimulating hormone (FSH) promotes differentiation of osteoclasts and that osteoclasts and osteoclast precursors express follicle stimulating hormone receptor (FSHR). As such, FSHR modulators (FSHRMs) and FSH modulators (FSHMs) find use in preventing differentiation of osteoclasts.

As such, FSHRM or FSHM compositions decrease the activity of osteoclasts. FSHRM and FSHM compositions are able to decrease osteoclast differentiation and bone resorption, including osteoclast differentiation and bone resorption promoted by a variety of agents.

By "follicle stimulating hormone receptor modulator", "FSHRM" and grammatical equivalents herein is meant a compound that reduces signaling or prevents signaling by the follicle stimulating hormone receptor. Such FSHRMs include, but are not limited to FSHR antagonists. They may include small molecules, peptides, proteins, antibodies, and the like.

By "follicle stimulating hormone modulator", "FSHM" and grammatical equivalents herein is meant a compound that reduces the bioactivity or bioavailability of FSH. Such FSHMs include, but are not limited to nucleic acids that reduce the level of FSH, small molecules, antibodies to FSH or other agents that bind FSH.

By "osteoclast differentiation" is meant the formation of a cell having at least one osteoclast activity from a cell that lacks the activity but is of the osteoclast lineage, and is therefore referred to as an "osteoclast precursor".

The term "osteoclast precursor" includes cells that give rise to osteoclasts without proliferation, as well as cells that go through one or more rounds of cell division to provide cells that give rise to osteoclasts without proliferation.

"Osteoclast activity" includes but is not limited to the ability to the ability to mobilize or break down bone or dentate mineral. Activities also include secretion of enzymes that modify signaling in the bone (MMP-9) and secretion of cytokines including nitric oxide, IL-1, TNFalpha, and IL-6 that further modify osteoblastic activity or bone survival in general.

By "decreasing osteoclast activity" is meant decreasing partially or completely one or more osteoclast activities, such as resorption, release of proteolytic enzymes, acid secretion and adhesion "Decreasing osteoclast activity" also includes inhibiting osteoclast differentiation (i.e., inhibiting osteoclastogenesis), whereby a precursor cell is kept from differentiating and obtaining the ability to exert an osteoclast activity.

By "osteoclast activation" is meant the promotion or induction of osteoclast activity.

Modulation of Osteoclast and Osteoblast Activity

In a preferred embodiment the method includes a method of modulating osteoclast activity. Also, the method includes modulation of osteoblast activity through signals that couple the activity of these two cell types.

In one aspect, the invention provides compositions and methods for decreasing osteoclast activity in a cell population comprising at least one osteoclast or osteoclast precursor cell. The methods involve contacting the osteoclast or osteoclast precursor cell with an FSHRM composition, whereby contact with an FSHRM composition decreases osteoclast activity.

In one aspect, the invention provides compositions and methods for decreasing osteoclast activity in a cell population comprising at least one osteoclast or osteoclast precursor cell. The methods involve providing an FSHM composition that reduces the bioavailability or bioactivity of FSH, including circulating FSH in the animal.

Cell populations may be in vivo or in vitro populations. Preferred cell populations are in vivo cell populations that include osteoclasts and bone marrow-derived macrophage precursor cells, which are precursors of osteoclasts.

By "contacting with an FSHRM composition" is meant providing the FSHRM composition to the cell in such a manner and in such an amount as to effect physical contact between the FSHRM composition and the cell.

"Providing an FSHRM composition to the vicinity of" means providing an FSHRM composition within an effective distance of the reference site. "Effective distance" means a distance within which the FSHRM composition can exert a bioactivity, particularly the ability to decrease osteoclast activity at the reference site. Providing can be done, for example, by local delivery, oral delivery, systemic delivery, etc. The FSHRM composition need not be directly delivered within the effective distance of the reference site to be "provided to the vicinity" of the reference site. The effective distance will vary with the nature of the FSHRM composition, the amount and formulation of the FSHRM composition used, and the nature of the tissue, but will be readily determined with standardizing experiments.

"Providing an FSHM composition" means administering an FSHM composition such that levels of bioactive or bioavailable FSH are reduced. Importantly, FSHMs may be administered in the vicinity of the osteoclast or at a site remote from the osteoclast. There is no requirement that the FSHMs interact with the FSHR or osteoclast cells because removing or reducing circulating levels of bioactive or bioavailable FSH will result in increased bone mineral density (see examples and FIG. 16).

Modulation of Signal Transduction in Osteoclasts and Osteoblasts

In one aspect, the invention provides compositions and methods for modulating signal transduction in osteoclasts and osteoclast precursor cells. The methods involve contacting osteoclasts or osteoclast precursor cells with an FSHRM composition. The methods may be used to decrease osteoclast activity.

In one embodiment, the invention provides methods for inhibiting FSHR signaling in osteoclast and osteoclast precursor cells. The methods involve contacting osteoclasts or osteoclast precursor cells with an FSHRM composition.

In one embodiment, the invention provides methods for inhibiting or reducing FSH signaling. The methods involve providing a FSHM that reduces the bioavailability or bioactivity of FSH.

Treatment of Bone Loss Disorders

In one aspect, the invention provides compositions and methods for the treatment of bone loss disorders. "Bone loss disorders" include conditions and diseases wherein the inhibition of bone loss and/or the promotion of bone formation is desirable. Among such conditions and diseases are osteoporosis, osteomyelitis, Paget's disease, periodontitis, hypercalcemia, osteonecrosis, osteosarcoma, osteolyic metastases, familial expansile osteolysis, prosthetic loosening, periprostetic osteolysis, cleiodocranial dysplasia (CCD), osteoporosis from arthritides, and bone loss due to metastatic disease and humoral hypercalcemia. The methods involve administering a therapeutic amount of an FSHRM and/or a FSHM composition to a patient having a bone loss disorder. Also provided are methods for decreasing osteoclast activity in patients having a bone loss disorder using an FSHRM and/or a FSHM composition.

It is understood that an FSHRM composition and/or a FSHM composition may be used alone or in conjunction with other factors for the treatment of bone disorders. In one embodiment, an FSHRM or FSHM composition is used in combination with other osteoclast inhibitors, or agents that find use in treating bone disorders as described herein. Several agents that are approved for treating bone disorders include estrogen replacement therapies, including estrogens such as Climara®, Estrace®, Estraderm®, Estratab®, Menostar™, Ogen®, Ortho-Est®, Premarin®, Vivelle®, and others, estrogens and progestins, such as Activella™, Fem-Hrt®, Premphase®, Prempro®, and others, selective estrogen receptor modulators (raloxifene (Evista®)), two bisphosphonates, alendronate and risedronate, calcitonin and parathyroid hormone, including Teriparatide (PTH (1034) (brand name Forteo®), and additional agents, such as cathepsin K inhibitors, integrin inhibitors, src inhibitors, and V-ATPase inhibitors, including bafilomycin. Also, additional bisphosphonates (zoledronic acid, clodronate, tiludronate, pamidronate, etidronate, ibandronate) and partial estrogen agonists and antagonists including genistein, daidzein and related phytoestrogens and tamoxifen. Also, bone binding transition metals gallium thallium and indium, inhibitors of chloride channel activity including n53736.

In another preferred embodiment, the invention provides methods for treating a variety of osteoporosis disorders, such as primary osteoporosis, endocrine osteoporosis (hyperthyroidism, hyperparathyroidism, Cushing's syndrome, and acromegaly), hereditary and congenital forms of osteoporosis (osteogenesis imperfecta, homocystinuria, Menkes' syndrome, and Rile-Day syndrome) and osteoporosis due to immobilization of extremities. Also provided are methods for decreasing osteoclast activity in patients having an osteoporosis disorder. The methods involve administering an FSHRM and/or an FSHM composition to a patient having an osteoporosis disorder.

In another preferred embodiment, the invention provides methods for treating osteomyelitis, or an infectious lesion in bone leading to bone loss. Also provided are methods for decreasing osteoclast activity in patients having osteomyelitis, or an infectious lesion in bone leading to bone loss. The methods involve administering an FSHRM and/or an FSHM composition to a patient having osteomyelitis, or an infectious lesion in bone leading to bone loss.

In another preferred embodiment, the invention provides methods for treating hypercalcemia, such as resulting from solid tumors (breast, lung and kidney) or hematologic malignancies (multiple myeloma, lymphoma and leukemia), idiopathic hypercalcemia, and hypercalcemia associated with hyperthyroidism and renal function disorders. In another preferred embodiment, the invention provides methods for treating osteonecrosis, or bone cell death, associated with traumatic injury or nontraumatic necrosis associated with Gaucher's disease, sickle cell anemia, systemic lupus erythematosus and other conditions. In another preferred embodiment, the invention provides methods for inhibiting bone loss attendant rheumatoid arthritis and other arthritides. In another preferred embodiment, the invention provides methods for treating periprosthetic osteolysis. In another preferred embodiment, the invention provides methods for treating bone loss due to osteolytic metastasis and humoral hypercalcemia of malignancy.

FSHRM Compositions

As noted above, FSHRMs of the invention can include a variety of different types of molecules including those that antagonize the FSH receptor or otherwise reduce FSH receptor signaling. Such FSHRMs include small molecules, proteins peptides, nucleic acids, antibodies and the like. For example, antibodies to FSH and FSH receptor are known in the art. See Zijlstra-Westhoff et al. J. Reprod. Immunol. 1998 July; 38(2): 139-54, which is expressly incorporated herein by reference. Likewise, nucleic acids encoding FSH and the FSH receptor are known. Thus, antisense molecules directed to either or both find use in the invention. Similarly, siRNA directed to the FSH receptor finds use in the invention to reduce the level of FSH receptor on osteoclasts thereby reducing osteoclast development or differentiation. In addition, Arey et al. have recently described a novel synthetic molecule capable of inhibiting the action of FSH. This compound (7-[4-[Bis-(2-carbamoyl-ethyl)-amino]-6-chloro-(1,3,5)-triazin-2-ylamino)-4-hydroxy-3-(4-methoxy-phenylazo)-naphthalene]-2-sulfonic acid, sodium salt) is a selective, noncompetitive inhibitor of the FSHR and is described in more detail Arey et al (Endocrinology, 2002 October; 143 (10):3822-9), which is expressly incorporated herein by reference. In addition, U.S. Pat. No. 6,426,357 describes a class of small molecule thiazolidinone FSH receptor antagonists.

The disclosure of this patent is expressly incorporated herein by reference for this teaching. In addition, such agents may be delivered by a fusion construct to a bisphosphonate or like compound to target it to bone or to TAT, a short peptide for intracellular delivery (Methods. 2001 July; 24(3):247-56; Methods Enzymol. 2001; 332:36-49, which are expressly incorporated herein by reference). Antibodies, including those currently in use for in vitro studies could be included.

FSHM Compositions

As noted above, FSHMs of the invention can include a variety of different types of molecules including those that reduce, or remove bioactive or bioavailable FSH. In a preferred embodiment the FSHM compositions reduce FSH by at least 10%, more preferably at least 20%, more preferably at least 30%, more preferably at least 40%, more preferably at least 50%, more preferably at least 60%, more preferably at least 70%, more preferably at least 80%, more preferably at least 90%. FSHMs include small molecules, proteins peptides, nucleic acids, antibodies and the like. For example, antibodies to FSH are known in the art. See Zijlstra-Westhoff et al. J. Reprod. Immunol. 1998 July; 38(2):139-54, which is expressly incorporated herein by reference. Likewise, nucleic acids encoding FSH are known (see U.S. Pat. No. 5,639,640, which is expressly incorporated herein by reference). See also Gen Bank accession number NM_000510, which is expressly incorporated herein by reference. Thus, antisense molecules directed to FSH find use in the invention. Similarly, siRNA directed to the FSH finds use in the invention to reduce the level of FSH thereby reducing osteoclast development or differentiation.

In addition, modulation of GnRH action also results in reduced circulating FSH (see Kraus S, Naor Z, Seger R, Arch Med Res. 2001 November-December; 32 (6):499-509). There are GnRH antagonists such as zoladex, widely used for treating prostate cancer, that reduce FSH levels and find use in the method. Similarly, new inhibitors of GnRH production or action, including antibodies to the GnRH or GnRH receptor, find use in reducing FSH levels.

In addition U.S. Pat. No. 6,583,179, which is expressly incorporated herein by reference, describes a series of novel substituted aminoalkylamide derivatives that are antagonists of FSH.

Methods of Screening for FSHRMs

Suitable FSHRMs and or FSHMs for use in the compositions and methods provided herein have a variety of characteristics, and may be identified in a number of ways.

FSHRMs may be identified by their ability to inhibit osteoclast activity. For example, putative FSHRM may be screened by incubation with osteoclast precursor cells under conditions known to promote osteoclast differentiation. The method comprises incubating an osteoclast precursor for a time and under conditions suitable for differentiation with FSH in the absence and presence of a putative FSHRM, and measuring the formation of mature osteoclasts, wherein a decrease in the number of mature osteoclasts in the presence of the putative agent is indicative of the identification of a FSHRM. Conditions include, e.g. the presence of RANK-L. Formation of osteoclasts may be detected, e.g. with TRAP as described herein. For example, the method may include using RAW264.7 cells (osteoclast precursors) or bone marrow precursor cells that can be incubated with compounds in the presence of receptor activator for NFkB ligand (RANK-L). Tartrate-resistant acid phosphatase-positive osteoclasts form that can be counted either manually or by computer assisted programs. In addition, the method preferably includes the pit assay (see examples). Other assays include monitoring characteristic osteoclastic proteins including cathepsin K, tratrate resistant acid phosphatase (TRAP) (as described herein), and the TCIRG variant of the large membrane subunit of the H+-ATPase. All of these are highly specific for the osteoclast. Other characteristic but less specific proteins include MMP-9 and alphaVbeta3 integrin.

FSHRMs may also be identified by their ability to modulate bone resorption in vivo by methods as known in the art. For example, bone resorption in vivo and its modulation is assessed by examining effects of compounds in rodents (mice and rats) following ovariectomy or orchidectomy, PTH treatment or immobilization. 6 weeks after ovariectomy or orchidectomy, there is bone loss up to 10%, which should be reversed by the administration of an osteoclast inhibitory agent, such as an FSHRM. Bone loss is quantitated histomorphometrically or by bone mineral density measurements (Piximus) or by microCT examination of 3-D structural elements. These are well known straightforward techniques.

Methods of Screening for FSHMs

FSHMs may be identified by their ability to inhibit osteoclast activity. For example, putative FSHM may be screened by incubation with osteoclast precursor cells under conditions known to promote osteoclast differentiation. The method comprises incubating an osteoclast precursor for a time and under conditions suitable for differentiation with FSH in the absence and presence of a putative FSHM, and measuring the formation of mature osteoclasts, wherein a decrease in the number of mature osteoclasts in the presence of the putative agent is indicative of the identification of a FSHM. Conditions include, e.g. the presence of RANK-L. Formation of osteoclasts may be detected, e.g. with TRAP as described herein. For example, the method may include using RAW 264.7 cells (osteoclast precursors) or bone marrow precursor cells that can be incubated with compounds in the presence of receptor activator for NFkB ligand (RANK-L). Tartrate-resistant acid phosphatase-positive osteoclasts form that can be counted either manually or by computer assisted programs. In addition, the method preferably includes the pit assay (see examples). Other assays include monitoring characteristic osteoclastic proteins including cathepsin K, tratrate resistant acid phosphatase (TRAP) (as described herein), and the TCIRG variant of the large membrane subunit of the H+-ATPase. All of these are highly specific for the osteoclast. Other characteristic but less specific proteins include MMP-9 and alphaVbeta3 integrin.

FSHMs may also be identified by their ability to modulate bone resorption in vivo by methods as known in the art. For example, bone resorption in vivo and its modulation is assessed by examining effects of compounds in rodents (mice and rats) following ovariectomy or orchidectomy, PTH treatment or immobilization. 6 weeks after ovariectomy or orchidectomy, there is bone loss up to 10%, which should be reversed by the administration of an osteoclast inhibitory agent, such as an FSHM. Bone loss is quantitated histomorphometrically or by bone mineral density measurements (Piximus) or by microCT examination of 3-D structural elements. These are well known straightforward techniques.

In addition, methods include contacting the source of FSH, e.g. cells that produce or secrete FSH, with a candidate FSHM and measuring the resulting production of FSH. In this embodiment, FSHMs are identified by their ability to reduce synthesis or secretion of FSH.

In an additional embodiment agents are provided and circulating levels of FSH are measured. Again, FSHMs according to this embodiment, result in reduced circulation of FSH. FHS can be measured by ELISA, immunoprecipitation, immunoblotting or radioimmunoassay, and the like, as is known in the art.

In an additional embodiment, FSHMs may be identified by screening for agents that reduce the activity of FSH promoter by methods known in the art.

Antibodies to FSH or FSHR

The present invention further provides anti-FSH or anti-FHSR antibodies. As noted previously, nucleic acids encoding FSH or the FSHR are known and find use in enabling a variety of antibodies. Exemplary antibodies include polyclonal, monoclonal, humanized, bispecific, and heteroconjugate antibodies.

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the FSH or FSHR polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the FSH or FSHR polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing c ells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51-63].

The culture medium in which the hybridoma cells are cultured can then be assayed for the presence of monoclonal antibodies directed against FSH or FSHR. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Means of Administering FSHRM and FSHM Compositions

It will be appreciated that different means of application are preferred for the different intended uses of FSHRM or FSHM compositions disclosed herein. Further, some intended uses may be achieved by more than one means of application.

For example, (i) systemic application is preferred for the treatment of osteoporosis and periodontitis, (ii) intra-articular application is preferred for the treatment of periprosthetic osteolysis and the osteolysis attendant arthritis, and (iii) local application is preferred for the reconstruction of bone defects in cranio-maxillofacial surgery, implant and prosthesis support, fracture healing, and periodontitis. For example, see U.S. Pat. No. 6,716,883, U.S. Pat. No. 6,620,406, U.S. Pat. No. 4,446,578, U.S. Pat. No. 6,428,803, and U.S. Pat. No. 5,069,905, each of which is expressly incorporated herein by reference.

Nucleic Acids, Expression Vectors, and Methods of Introduction

When the synthesis or delivery of the peptides is via nucleic acids encoding the subject peptides, the nucleic acids are cloned into expression vectors and introduced into cells or a host. The expression vectors are either self-replicating extrachromosomal vectors or vectors that integrate into the host chromosome, for example vectors based on retroviruses, vectors with site specific recombination sequences, or by homologous recombination. Generally, these vectors include control sequences operably linked to the nucleic acids encoding the peptides. By "control sequences" is meant nucleic acid sequences necessary for expression of the subject peptides in a particular host organism. Thus, control sequences include sequences required for transcription and translation of the nucleic acids, including, but not limited to, promoter sequences, enhancer or transcriptional activator sequences, ribosomal binding sites, transcriptional start and stop sequences; polyadenylation signals; etc.

A variety of promoters are useful in expressing the peptides of the present invention. The promoters may be constitutive, inducible, and/or cell specific and may comprise natural promoters, synthetic promoters (e.g. tTA tetracycline inducible promoters), or hybrids of various promoters. Promoters are chosen based on, among others, the cell or organism in which the proteins are to be expressed, the level of desired expression, and regulation of expression. Suitable promoters are bacterial promoters (e.g., pL 1 phage promoter, tac promoter, lac lac promoter, etc.); yeast based promoters (e.g., GAL4 promoter, alcohol dehydrogenase promoter, tryptophane synthase promoter, copper inducible CUPI promoter, etc.), plant promoters (e.g., CaMV S35, nopoline synthase promoter, tobacco mosaic virus promoter, etc), insect promoters (e.g., *Autographa* nuclear polyhedrosis virus, *Aedes* DNV viral p& and p61, hsp70, etc.), and promoters for expression mammalian cells (e.g., ubiquitin gene promoter, ribosomal gene promoter, β-globin promoter, thymidine kinase promoter, heat shock protein promoters, and ribosomal gene promoters, etc.), and particularly viral promoters, such as cytomegalovirus (CMV) promoter, simian virus (SV40) promoter, and retroviral promoters.

By "operably linked" herein is meant that a nucleic acid is placed into a functional relationship with another nucleic acid. In the present context, operably linked means that the control sequences are positioned relative to the nucleic acid sequence encoding the subject peptides in such a manner that expression of the encoded peptide occurs. The vectors may comprise plasmids or comprise viral vectors, for example retroviral vectors, which are useful delivery systems if the cells are dividing cells, or lentiviral and adenoviral vectors if the cells are non-dividing cells. Particularly preferred are self-inactivating retroviral vectors (SIN vectors), which have inactivated viral promoters at the 3'-LTR, thereby permitting control of expression of heterologous genes by use of non-viral promoters inserted into the viral vector (see for example, Hoffman et al. Proc. Natl. Acad. Sci. USA 93: 5185 (1996). As will be appreciated by those in the art, modifications of the system by pseudotyping allows use of retroviral vectors for all eukaryotic cells, particularly for higher eukaryotes (Morgan, R. A. et al. J. Virol. 67: 4712-21 (1993); Yang, Y. et al. Hum. Gene Ther. 6: 1203-13 (1995)).

In addition, the expression vectors also contain a selectable marker gene to allow selection of transformed host cells. Generally, the selection will confer a detectable phenotype that enriches for cells containing the expression vector and further permits differentiation between cells that express and do not express the selection gene. Selection genes are well known in the art and will vary with the host cell used. Suitable selection genes included genes that render the cell resistant to a drug, genes that permit growth in nutritionally deficient media, and reporter genes (e.g. β-galactosidase, fluorescent proteins, glucouronidase, etc.), all of which are well known in the art and available to the skilled artisan.

There are a variety of techniques available for introducing nucleic acids into viable cells. By "introduced" into herein is meant that the nucleic acid enters the cells in a manner suitable for subsequent expression of the nucleic acid. Techniques for introducing the nucleic acids will vary depending on whether the nucleic acid is transferred in vitro into cultured cells or in vivo into the cells of the intended host organism and the type of host organism. Exemplary techniques for introducing the nucleic acids in vitro include the use of liposomes, Lipofectin®, electroporation, microinjection, cell fusion, DEAE dextran, calcium phosphate precipitation, and biolistic particle bombardment. Techniques for transfer in vivo include direct introduction of the nucleic acid, use of viral vectors, typically retroviral vectors, and liposome mediated transfection, such as viral coated liposome mediated transfection. The nucleic acids expressing the peptides of the present invention may exist transiently or stably in the cytoplasm or stably integrate into the chromosome of the host (i.e., through use of standard regulatory sequences, selection markers, etc.). Suitable selection genes and marker genes are used in the expression vectors of the present invention.

In some situations, it is desirable to include an agent that targets the target cells or tissues, such as an antibody specific for a cell surface protein or the target cell, a ligand for a receptor on the target cell, a lipid component on the cell membrane, or a carbohydrate on the cell surface. If liposomes are employed, proteins that bind a cell surface protein which is endocytosed may be used for targeting and/or facilitating uptake. These include as non-limiting examples, capsid proteins or fragments thereof tropic for a particular cell types, antibodies for proteins which undergo internalization (see Wu et al. J. Biol. Chem. 262: 4429-4432 (1987); Wagner et al. Proc. Natl. Acad. Sci. USA 87: 3410-3414 (1990)), and proteins that direct localization (e.g., antibody to transferrin receptor for targeting to brain) or enhance in vivo half-life.

Expression is done in a wide range of host cells that span prokaryotes and eukaryotes, including bacteria, yeast, plants, insects, and animals. The peptides of the present invention may be expressed in, among others, *E. coli., Saccharomyces cerevisiae, Saccharomyces pombe*, Tobacco or *Arabidopsis* plants, insect Schneider cells, and mammalian cells, such as COS, CHO, HeLa, and the like, either intracellularly or in a secreted form by fusing the peptides to an appropriate signal peptide. Secretion from the host cell may be done by fusing the DNA encoding the peptide and a DNA encoding a signal peptide. Secretory signals are well known in the art for bacteria, yeast, insects, plants, and mammalian systems. Nucleic acids expressing the peptides may be inserted into cells, for example stem cells for tissue expression or bacteria for gut expression, and the cells transplanted into the host to provide an in vivo source of the peptides.

Purified Peptides

In a preferred embodiment, the FSHRM or FSHM peptides of the present invention may be purified or isolated after synthesis or expression. By "purified" or "isolated" is meant free from the environment in which the peptide is synthesized or expressed and in a form where it can be practically used. Thus purified or isolated is meant that the peptide or its derivative is substantially pure, i.e., more than 90% pure, preferably more than 95% pure, and preferably more than 99% pure. The peptides and derivatives thereof may be purified and isolated by way known to those skilled in the art, depending on other components present in the sample. Standard purification methods include electrophoretic, immunological, and chromatographic techniques, including ion exchange, hydrophobic, affinity, size exclusion, reverse phase HPLC, and chromatofocusing. The proteins may also be purified by selective solubility, for instance in the presence of salts or organic solvents. The degree of purification necessary will vary depending on use of the subject peptides. Thus, in some instances no purification will be necessary.

For the most part, the compositions used will comprise at least 20% by weight of the desired product, more usually at least about 75% by weight, preferably at least about 95% by weight, and usually at least about 99.5% by weight, relative to contaminants related to the method of product preparation, the purification procedure, and its intended use, for example with a pharmaceutical carrier for the purposes of therapeutic treatment. Usually, the percentages will be based upon total protein.

Pharmaceutical Formulations, Dosage Forms, Dosages, and Methods of Administration The subject compositions, either alone or in combination, may be used in vitro, ex vivo, and in vivo depending on the particular application. In accordance, the present invention provides for administering a pharmaceutical composition comprising a pharmaceutically acceptable carrier and a pharmacologically effective amount of one or more of the subject peptides, or suitable salts thereof. The pharmaceutical composition may be formulated as powders, granules, solutions, suspensions, aerosols, solids, pills, tablets, capsules, gels, topical crèmes, suppositories, transdermal patches, etc.

As indicated above, pharmaceutically acceptable salts of the peptides is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any of standard pharmaceutically accepted carriers known to those of ordinary skill in the art in formulating pharmaceutical compositions. Thus, the subject peptides, by themselves, such as being present as pharmaceutically acceptable salts, or as conjugates, or nucleic acid vehicles encoding such peptides, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients. Additionally, the formulations may include bactericidal agents, stabilizers, buffers, emulsifiers, preservatives, sweetening agents, lubricants, or the like. If administration is by oral route, the oligopeptides may be protected from degradation by using a suitable enteric coating, or by other suitable protective means, for example internment in a polymer matrix such as microparticles or pH sensitive hydrogels.

Suitable formulations may be found in, among others, Remington's Pharmaceutical Sciences, 17th edition, Mack Publishing Co., Philadelphia, Pa., 1985 and Handbook of Pharmaceutical Excipients, 3rd Ed, Kibbe, A. H. ed., Washington D.C., American Pharmaceutical Association, 2000; hereby incorporated by reference in their entirety. The pharmaceutical compositions described herein can be made in a manner well known to those skilled in the art (e.g., by means conventional in the art, including mixing, dissolving, granulating, levigating, emulsifying, encapsulating, entrapping or lyophilizing processes).

Additionally, the peptides may also be introduced or encapsulated into the lumen of liposomes for delivery and for extending life time of the peptide formulations ex vivo or in vivo. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see for example, U.S. Pat. No. 5,833,948).

Cationic lipids are also suitable for forming liposomes. Generally, the cationic lipids have a net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3,-ditetradecycloxy)propyl]-N,N-dimethyl-N-N-hydroxyethylammonium bromide; N-[1-(2,3-dioleyloxy)propyl]-N,N-dimethyl-N-hydroxy ethylammonium bromide; N-[1-(2,3-dioleyloxy)propyl]-N,N,N-trimethylammonium chloride; 3-[N-(N',N'-dimethylaminoethane)carbamoyl]cholesterol; and dimethyldioctadecylammonium.

Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH (see for example, U.S. Pat. Nos. 4,789,633 and 4,873,089). Generally, pH sensitive liposomes are acid sensitive. Thus, fusion is enhanced in physiological environments where the pH is mildly acidic, for example the environment of a lysosome, endosome and inflammatory tissues. This property allows direct release of the liposome contents into the intracellular environment following endocytosis of liposomes (see Mizoue, T. Int. J. Pharm. 237: 129-137 (2002)).

Another form of fusogenic liposomes comprises liposomes that contain a fusion enhancing agent. That is, when incorporated into the liposome or attached to the lipids, the agents enhance fusion of the liposome with other cellular membranes, thus resulting in delivery of the liposome contents into the cell. The agents may be fusion enhancing peptides or proteins, including hemagglutinin HA2 of influenza virus (Schoen, P. Gene Ther. 6: 823-832 (1999)); Sendai virus envelope glycoproteins (Mizuguchi, H. Biochem. Biophys. Res. Commun. 218: 402-407 (1996)); vesicular stomatitis virus envelope glycoproteins (VSV-G) glycoprotein (Abe, A. et al. J Virol 72: 6159-63 (1998)); peptide segments or mimics of fusion enhancing proteins; and synthetic fusion enhancing peptides (Kono, K. et al. Biochim. Biophys. Acta. 1164: 81-90 (1993); Pecheur, E. I. Biochemistry 37: 2361-71 (1998); U.S. Pat. No. 6,372,720).

Liposomes also include vesicles derivatized with a hydrophilic polymer, as provided in U.S. Pat. Nos. 5,013,556 and 5,395,619, hereby incorporated by reference, (see also, Kono, K. et al. J. Controlled Release 68: 225-35 (2000); Zalipsky, S. et al. Bioconjug. Chem. 6: 705-708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization (see Wu et al, supra; Wagner et al., supra), may be used for targeting and/or facilitating uptake of the liposomes to specific cells or tissues.

Liposomes are prepared by ways well known in the art (see for example, Szoka, F. et al. Ann. Rev. Biophys. Bioeng. 9: 467-508 (1980)). One typical method is the lipid film hydration technique in which lipid components are mixed in an organic solvent followed by evaporation of the solvent to generate a lipid film. Hydration of the film in aqueous buffer solution, preferably containing the subject peptide or nucleic acid, results in an emulsion, which is sonicated or extruded to reduce the size and polydispersity. Other methods include reverse-phase evaporation (see Pidgeon, C. et al. Biochemistry 26: 17-29 (1987); Duzgunes, N. et al. Biochim. Biophys. Acta. 732: 289-99 (1983)), freezing and thawing of phospholipid mixtures, and ether infusion.

In another preferred embodiment, the carriers are in the form of microparticles, microcapsules, microspheres and nanoparticles, which may be biodegradable or non-biodegradable (see for example, Microencapsulates: Methods and Industrial Applications, Drugs and Pharmaceutical Sciences, Vol 73, Benita, S. ed, Marcel Dekker Inc., New York, 1996; incorporated by reference). As used herein, microparticles, micro spheres, micro capsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. As used herein, microparticles have a particle size range of about 1 to about >1000 microns. Nanoparticles have a particle size range of about 10 to about 1000 nm.

A variety of materials are useful for making microparticles. Non-biodegradable microcapsules and microparticles include, but not limited to, those made of polysulfones, poly (acrylonitrile-co-vinyl chloride), ethylene-vinyl acetate, hydroxyethylmethacrylate-methyl-methacrylate copolymers. These are useful for implantation purposes where the encapsulated peptide diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly($\beta$-hydroxybutyrate)), poly ($\beta$-ethyl glutamate), poly(DTH iminocarbony (bisphenol A iminocarbonate), poly (ortho ester), and polycyanoacrylate. Various methods for making microparticles containing the subject compositions are well known in the art, including solvent removal process (see for example, U.S. Pat. No. 4,389,330); emulsification and evaporation (Maysinger, D. et al. Exp. Neuro. 141: 47-56 (1996); Jeffrey, H. et al. Pharm. Res. 10: 362-68 (1993)), spray drying, and extrusion methods.

Another type of carrier is nanoparticles, which are generally suitable for intravenous administrations. Submicron and nanoparticles are generally made from amphiphilic diblock, triblock, or multiblock copolymers as is known in the art. Polymers useful in forming nanoparticles include, but are limited to, poly(lactic acid) (PLA; see Zambaux et al., J. Control Release 60: 179-188 (1999)), poly(lactide-co-glycolide), blends of poly(lactide-co-glycolide) and polycarprolactone, diblock polymer poly(l-leucine-block-1-glutamate), diblock and triblock poly(lactic acid) (PLA) and poly(ethylene oxide) (PEO) (see De Jaeghere, F. et al., Pharm. Dev. Technol.; 5: 473-83 (2000)), acrylates, arylamides, polystyrene, and the like. As described for microparticles, nanoparticles may be non-biodegradable or biodegradable. Nanoparticles may be also be made from poly(alkylcyanoacrylate), for example poly(butylcyanoacrylate), in which the peptide is absorbed onto the nanoparticles and coated with surfactants (e.g., polysorbate 80). Methods for making nanoparticles are similar to those for making microparticles and include, among others, emulsion polymerization in continuous aqueous phase, emulsification-evaporation, solvent displacement, and emulsification-diffusion techniques (see Kreuter, J. Nano-particle Preparation and Applications, In Microcapsules and nanoparticles in medicine and pharmacy," (M. Donbrow, ed.), pg. 125-148, CRC Press, Boca Rotan, Fla., 1991; incorporated by reference).

Hydrogels are also useful in delivering the subject agents into a host. Generally, hydrogels are cross linked, hydrophilic polymer networks permeable to a wide variety of drug compounds, including peptides. Hydrogels have the advantage of selective trigger of polymer swelling, which results in controlled release of the entrapped drug compound. Depending on the composition of the polymer network, swelling and subsequent release may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide), poly(N-isopropylacrylamide); poly(methacrylic acid-g-polyethylene glycol); polyacrylic acid and poly(oxypropylene-co-oxyethylene) glycol; and natural compounds such as chrondroitan sulfate, gelatin, or mixtures of synthetic and natural polymers, for example chitosan-poly(ethylene oxide). The polymers are cross linked reversibly or irreversibly to form gels embedded with the oligopeptides of the present invention (see for example, U.S. Pat. Nos. 6,451,346; 6,410,645; 6,432, 440; 6,395,299; 6,361,797; 6,333,194; 6,297,337 Johnson, O. et al., Nature Med. 2: 795 (1996); incorporated by reference in their entirety).

In one preferred embodiment, the gel polymers are acrylic acid polymers, preferably carbomers (e.g., carboxypolymethylene), such as Carbopol (e.g., Carbopol 420-430, 475, 488, 493, 910, 934P, 974P, and the like; Brock et al., Pharmacotherapy 14: 430-437 (1994)), which are non-linear polymers of acrylic acid cross linked with polyalkenyl polyether. Others types of carbomers include acrylic acids cross linked with polyfunctional compounds, such as polyallysucrose. In addition to the advantage of hydrating and swelling to a gel, which entraps the subject compounds and limits their release, carbomer gels are mucoadhesive.

The concentrations of the peptides or nucleic acid encoding therefore will be determined empirically in accordance with conventional procedures for the particular purpose. Generally, for administering the peptides ex vivo or in vivo for therapeutic purposes, the subject formulations are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms of the disorder or disease.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery of the agent, half-life of the agents, and efficacy of the agents. Stage of the disease to consider include whether the disease is acute or chronic, relapsing or remitting phase, and the progressiveness of the disease. Determining the dosages and times of administration for a therapeutically effective amount are well within the skill of the ordinary person in the art.

The toxicity and therapeutic efficacy are generally determined by cell culture assays and/or experimental animals, typically by determining a LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein.

Generally, in the case where formulations are administered directly to a host, the present invention provides for a bolus or infusion of the subject composition that will be administered in the range of about 0.1-50, more usually from about 1-25 mg/kg body weight of host. The amount will generally be adjusted depending upon the half-life of the peptide where the half life will generally be at least one minute, more usually at least about 10 min, desirably in the range of about 10 min to 12 h. Short half-lives are acceptable, so long as efficacy can be achieved with individual dosages, continuous infusion, or repetitive dosages. Formulations for administration may be presented in unit a dosage form, e.g., in ampules, capsules, pills, or in multidose containers or injectables.

Dosages in the lower portion of the range and even lower dosages may be employed, where the peptide has an enhanced half-life or is provided as a depot, such as a slow release composition comprising particles, a polymer matrix which maintains the peptide over an extended period of time (e.g., a collagen matrix, carbomer, etc.), use of a pump which continuously infuses the peptide over an extended period of time with a substantially continuous rate, or the like. The host or subject may be any mammal including domestic animals, pets, laboratory animals, primates, particularly humans subjects.

In addition to administering the subject peptide compositions directly to a cell culture in vitro, to particular cells ex vivo, or to a mammalian host in vivo, nucleic acid molecules (DNA or RNA) encoding the subject peptides may also be administered thereto, thereby providing an effective source of the subject peptides for the application desired. As described above, nucleic acid molecules encoding the subject peptides may be cloned into any of a number of well known expression plasmids (see Sambrook et al., supra) and/or viral vectors, preferably adenoviral or retroviral vectors (see for example, Jacobs et al., J. Virol. 66:2086-2095 (1992), Lowenstein, Bio/Technology 12:1075-1079 (1994) and Berkner, Biotechniques 6:616-624 (1988)), under the transcriptional regulation of control sequences which function to promote expression of the nucleic acid in the appropriate environment. Such nucleic acid-based vehicles may be administered directly to the cells or tissues ex vivo (e.g., ex vivo viral infection of cells for transplant of peptide producing cells) or to a desired site in vivo, e.g. by injection, catheter, orally (e.g., hybrogels), and the like, or, in the case of viral-based vectors, by systemic administration. Tissue specific promoters may optionally be employed, assuring that the peptide of interest is expressed only in a particular tissue or cell type of choice. Methods for recombinantly preparing such nucleic acid-based vehicles are well known in the art, as are techniques for administering nucleic acid-based vehicles for peptide production.

For the purposes of this invention, the method of administration is chosen depending on the condition being treated, the form of the subject compositions, and the pharmaceutical composition. Administration of the oligopeptides can be done in a variety of ways, including, but not limited to, cutaneously, subcutaneously, intravenously, orally, topically, transdermally, intraperitoneally, intramuscularly, nasally, and rectally (e.g., colonic administration). For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, oral administration can be accompanied by rectal or topical administration to the affected area. Alternatively, oral administration is used in conjunction with intravenous or parenteral injections.

The delivery systems also include sustained release or long term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above; pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provides a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The drug is contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating a disease condition, especially those manifesting recurring episodes or which are progressive in nature, by delivering the oligopeptides of the invention via systemic (e.g., intravenous or subcutaneous) or localized doses (e.g., intracerebroventricular) in a sustained, long term manner.

In one preferred embodiment, the method of administration is by oral delivery, in the form of a powder, tablet, pill, or capsule. Pharmaceutical formulations for oral administration may be made by combining one or more peptide with suitable excipients, such as sugars (e.g., lactose, sucrose, mannitol, or sorbitol), cellulose (e.g., starch, methyl cellulose, hydroxylmethyl cellulose, carboxymethyl cellulose, etc.), gelatin, glycine, saccharin, magnesium carbonate, calcium carbonate, polymers such as polyethylene glycol or polyvinylpyrrolidone, and the like. The pills, tablets, or capsules may have an enteric coating, which remains intact in the stomach but dissolves in the intestine. Various enteric coating are known in the art, a number of which are commercially available, including, but not limited to, methacrylic acid-methacrylic acid ester copolymers, polymer cellulose ether, cellulose acetate phathalate, polyvinyl acetate phthalate, hydroxypropyl methyl cellulose phthalate, and the like. Alternatively, oral formulations of the peptides are in prepared in a suitable diluent. Suitable diluents include various liquid form (e.g., syrups, slurries, suspensions, etc.) in aqueous diluents such as water, saline, phosphate buffered saline, aqueous ethanol, solutions of sugars (e.g. sucrose, mannitol, or sorbitol), glycerol, aqueous suspensions of gelatin, methyl cellulose, hydroxylmethyl cellulose, cyclodextrins, and the like. As used herein, diluent or aqueous solutions also include infant formula. In some embodiments, lipohilic solvents are used, including oils, for instance vegetable oils, peanut oil, sesame oil, olive oil, corn oil, safflower oil, soybean oil, etc.); fatty acid esters, such as oleates, triglycerides, etc.; cholesterol derivatives, including cholesterol oleate, cholesterol linoleate, cholesterol myristilate, etc.; liposomes; and the like.

In one embodiment, administration is done rectally. This may use formulations suitable for topical application in the form of salves, tinctures, cremes, or for application into the lumen of the intestine by use of compositions in the form of suppositories, enemas, foams, etc. Suppositories may contain conventional suppository bases such as cocoa butter, carbowaxes, polyethylene glycols, or glycerides, which are solid or semi-solid at room temperature but liquid at body temperature.

In yet another preferred embodiment, the administration is carried out cutaneously, subcutaneously, intraperitonealy, intramuscularly or intravenously. As discussed above, these are in the form of peptides dissolved or suspended in suitable aqueous medium, as discussed above. Additionally, the pharmaceutical compositions for injection may be prepared in lipophilic solvents, which include, but is not limited to, oils, such as vegetable oils, olive oil, peanut oil, palm oil soybean oil, safflower oil, etc; synthetic fatty acid esters, such as ethyl oleate or triglycerides; cholesterol derivatives, including cholesterol oleate, cholesterol linoleate, cholesterol myristilate, etc.; or liposomes, as described above. The compositions may be prepared directly in the lipophilic solvent or preferably, as oil/water emulsions, (see for example, Liu, F. et al. Pharm. Res. 12: 1060-1064 (1995); Prankerd, R. J. J. Parent. Sci. Tech. 44: 139-49 (1990); U.S. Pat. No. 5,651,991).

The delivery systems also include sustained release or long term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above; pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provides a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The drug is contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating an inflammatory disease condition, especially those manifesting recurring episodes or which are progressive in nature, by delivering the oligopeptides of the invention via systemic (e.g., intravenous or subcutaneous) or localized doses in a sustained, long term manner.

The present invention also encompasses the therapeutic combinations disclosed herein in the form of a kit or packaged formulation. A kit or packaged formulation as used herein includes one or more dosages of a subject peptide, and salts thereof, in a container holding the dosages together with instructions for simultaneous or sequential administration to a patient. For example, the package may contain the peptides along with a pharmaceutical carrier combined in the form of a powder for mixing in an aqueous solution, which can be ingested by the afflicted subject. Another example of packaged drug is a preloaded pressure syringe, so that the compositions may be delivered colonically. The package or kit includes appropriate instructions, which encompasses diagrams, recordings (e.g., audio, video, compact disc), and computer programs providing directions for use of the combination therapy. The foregoing descriptions of specific embodiments of the present invention have been presented for purposes of illustration and description. They are not intended to be exhaustive or to limit the invention to the precise forms disclosed, and obviously many modifications and variations are possible in light of the above teaching.

EXPERIMENTAL

FIG. 1 shows an agarose gel electrophoresis experiment following RT-PCR of total RNA extracted from RAW264.7 cells (RAW) or osteoclasts derived therefrom (OC), as indicated in the Materials and Methods section. The last lane also represents RT-PCR on mRNA derived from osteoblasts (not studied further). A 200 bp band was seen in all three cases. Lane 1 is the marker lane. The bands were subsequently extracted from the gel and sent for commercial DNA sequencing. The identical sequence (FIG. 1) for each PCR product matched 100% with the sequence of that region in the GeneBank database.

Having demonstrated that the FSH receptor mRNA was expressed in osteoclasts, we next (a) established the presence of the encoded protein and (b) demonstrated a function for the FSH receptor protein. The first objective was to determine if a specific polyclonal antibody detected the osteoclast FSH receptor, and if so, whether the receptor was localized to the cell membrane A confocal microscopic approach was used and cells were co-labeled with an antibody to a nuclear antigen to allow us to differentiate membrane staining from intracellular staining.

Figure 2A:
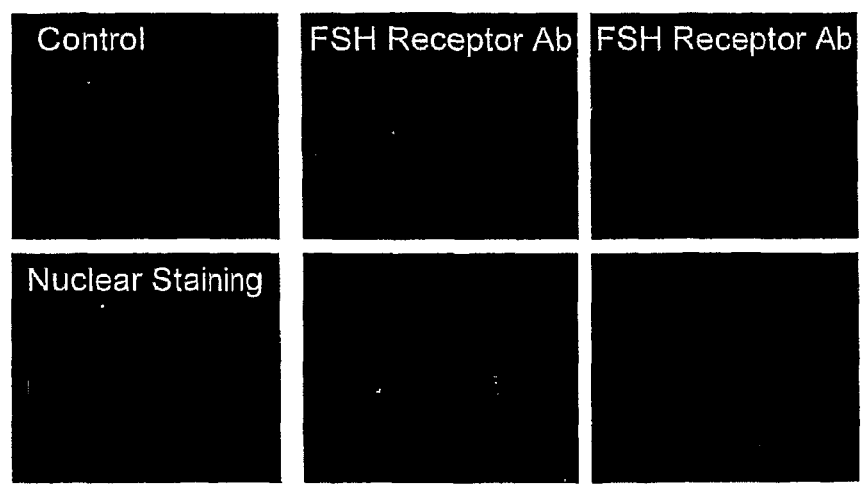
FIG. 2 shows immunolabeling of the FSH receptor using a highly specific polyclonal antibody to a defined epitope on the receptor (FIG. 2A). This was further confirmed in both RAW osteoclast precursors and osteoclasts derived therefrom using FACS analysis (FIG. 2B).
Figure 2B:
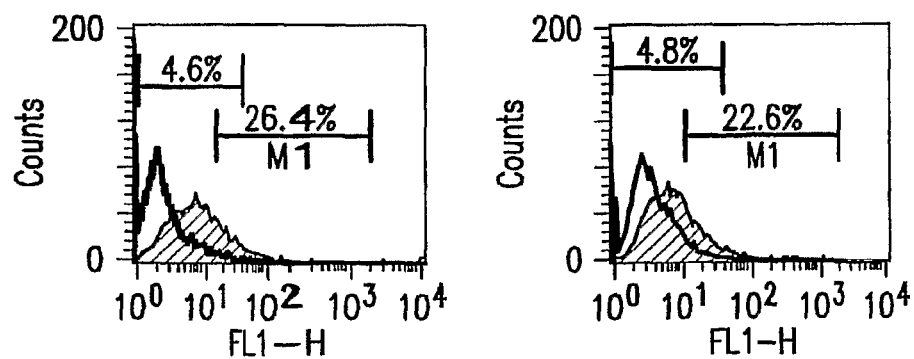
Figure 3:
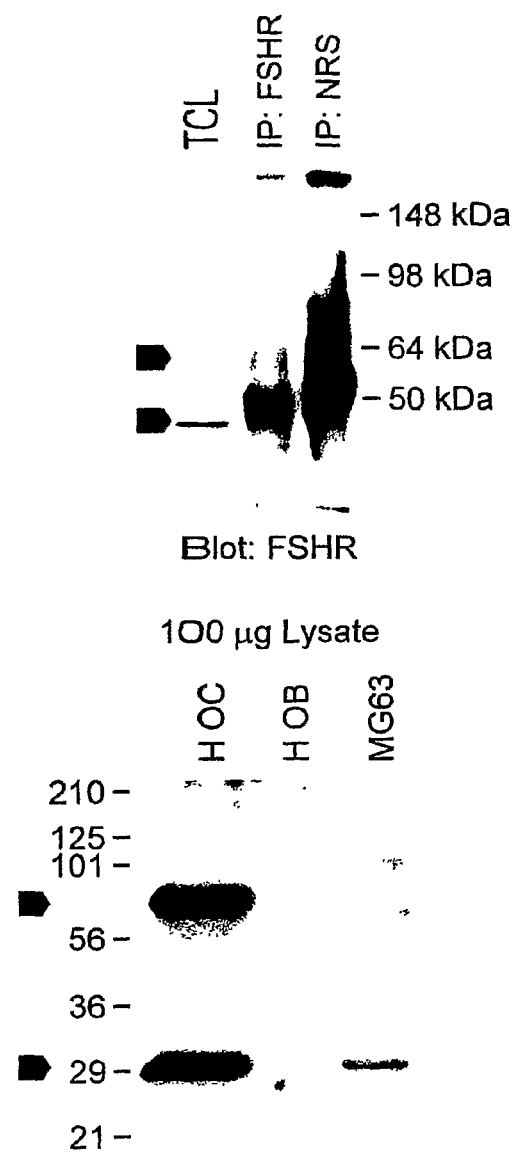
FIG. 3 likewise shows that the FSH receptor antibody detects the FSH receptor in immunoprecipitated extracts from RAW cell-derived osteoclasts.

The top panels show confocal micrographic images of osteoclasts after 1 and 4 days of RANK-L (60 ng/ml) treatment. The left panels are negative controls where a fluorescein-(green) or rhodamine-(red) tagged second antibody was added in the presence of non-immune goat serum and in the absence of the anti-FSH receptor or anti-nuclear antibodies, respectively (FIG. 2). No labeling was noted. The middle and rightmost of the top panels show green fluorescence. Note that in contrast to the bottom middle and rightmost panels where the red staining was centrally located, the green staining was mostly peripheral. This peripheral plasma membrane pattern would be expected for any G protein coupled receptor, including the calcitonin, thyroid stimulating hormone, or parathyroid hormone receptors (Martin et al, 2002). It is also of note that both osteoclast precursors seen at day 1 and mature osteoclasts at day 4 after RANK-L expressed the FSH receptor. This also was examined using FACS analysis and immunoprecipitation and immunoblotting (FIG. 3).

Together the RT-PCR and immunostaining data provides strong evidence for the presence of a FSH receptor on the surface of both osteoclast and osteoclast precursors. To date, FSH receptors have been demonstrated only on ovarian cells where they interact with circulating FSH to control estrogen secretion (Fortune, 2004). In that respect, to our knowledge, this is the first demonstration for an FSH receptor in any non-ovarian cell.

Figure 4A:
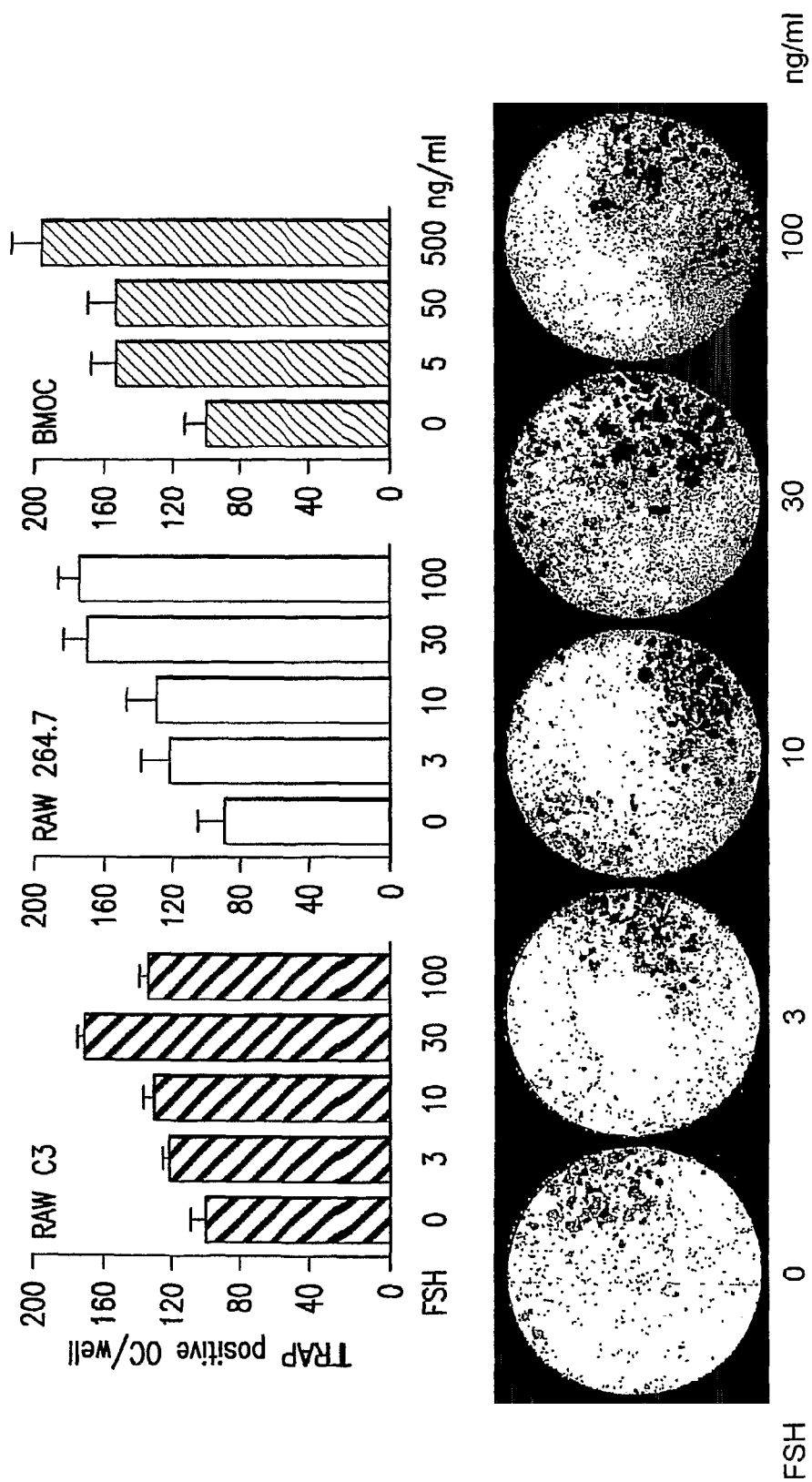
FIG. 4 shows functional effects of FSH on osteoclast formation, osteoclast differentiation markers, and osteoclast apoptosis. Using three separate cell types and two mice strains, it was demonstrated that FSH stimulated osteoclast differentiation (FIG. 4A), but not proliferation in vitro (FIG. 4B).
FIG. 4B shows the effect of various concentrations of FSH on the proliferation of RAW264.7 cells.

We next studied whether FSH could cause increased osteoclast formation. The rationale for these experiments, as explained in the Introduction, was to determine whether FSH, through its action on the FSH receptor on the osteoclast precursor could stimulate the formation of new osteoclasts. Thus, osteoclast precursors from various sources, notably purified bone marrow and RAW264.7 cells were incubated with RANK-L (50 or 100 ng/ml) and various concentrations of FSH (shown in FIGS. 4A and 4B). As noted before, RANK-L is a cytokine that is essential for osteoclast formation (Hofbauer and Schoppet, 2004). After 6 days, we stained the cells for TRAP to examine the formation of mature osteoclasts (again, TRAP or tartrate resistant acid phosphatase is an enzyme marker for osteoclasts).

First, we examined whether a single concentration of FSH (30 ng/ml) could further enhance the osteoclast formation from RAW264.7 cells by RANK-L (50 or 100 ng/ml). That was indeed the case (data not shown). We then examined whether the response was dependent upon FSH concentration. With both bone marrow cells and RAW264.7 cells, there was a 2-fold elevation of osteoclast formation in two experiments (FIG. 4). Together the studies demonstrated that FSH enhanced osteoclast formation.

Figure 5:
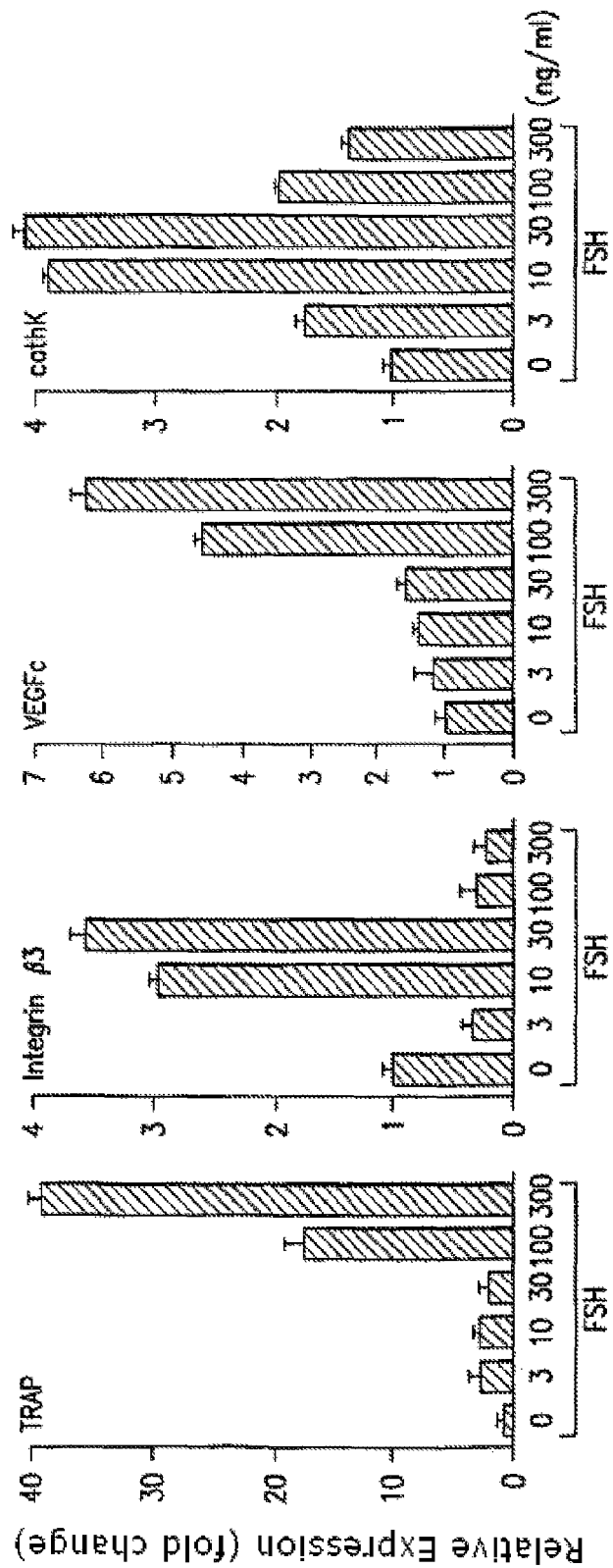
FIG. 5 shows functional effects of FSH on osteoclast formation and differentiation markers. It was demonstrated that traditional markers of osteoclast formation, notably the expression of tartrate-resistant acid phosphatase (TRAP), β3 integrin, cathepsin K and calcitonin receptors was stimulated with FSH in real time quantitative PCR studies.
Figure 6:
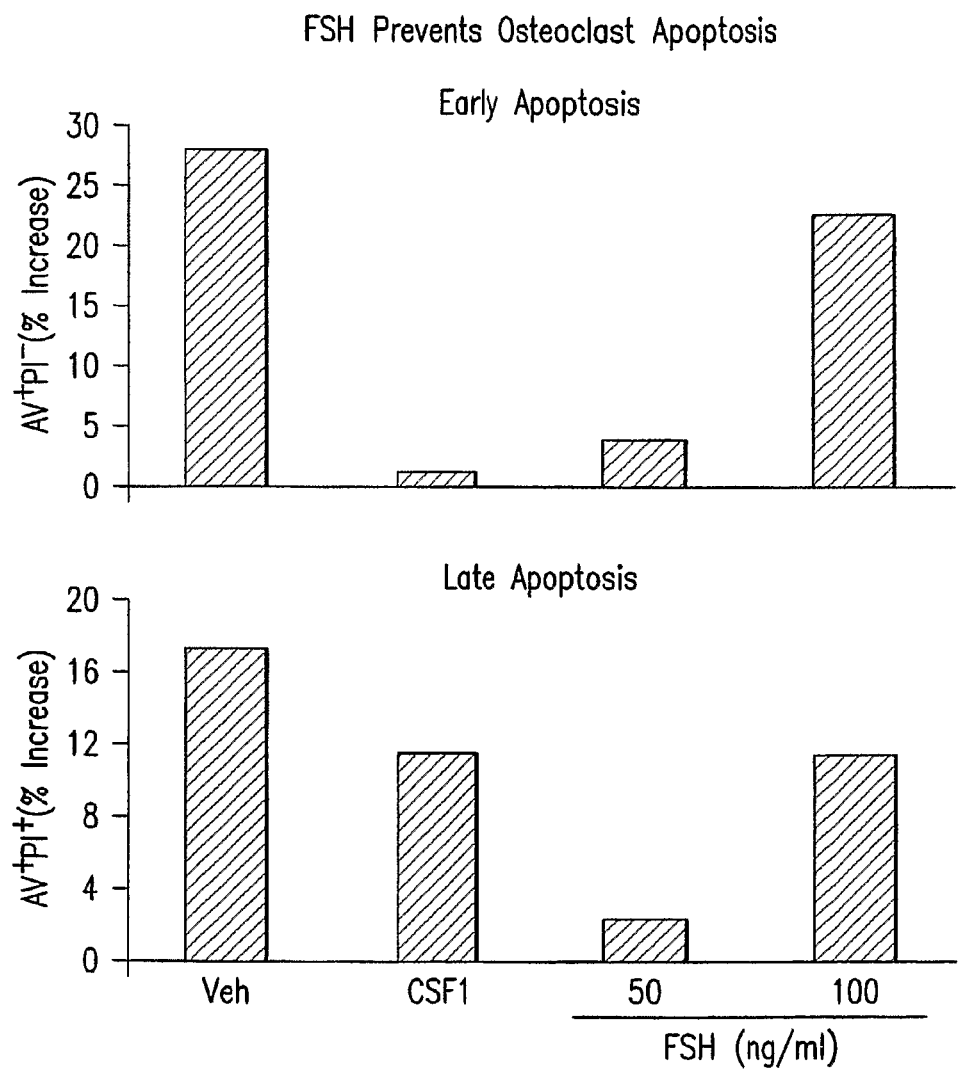
FIG. 6 shows functional effects of FSH on osteoclast apoptosis. It was demonstrated that apoptosis of osteoclast precursors measured by annexin V staining was reduced in the presence of FSH.
Figure 7:
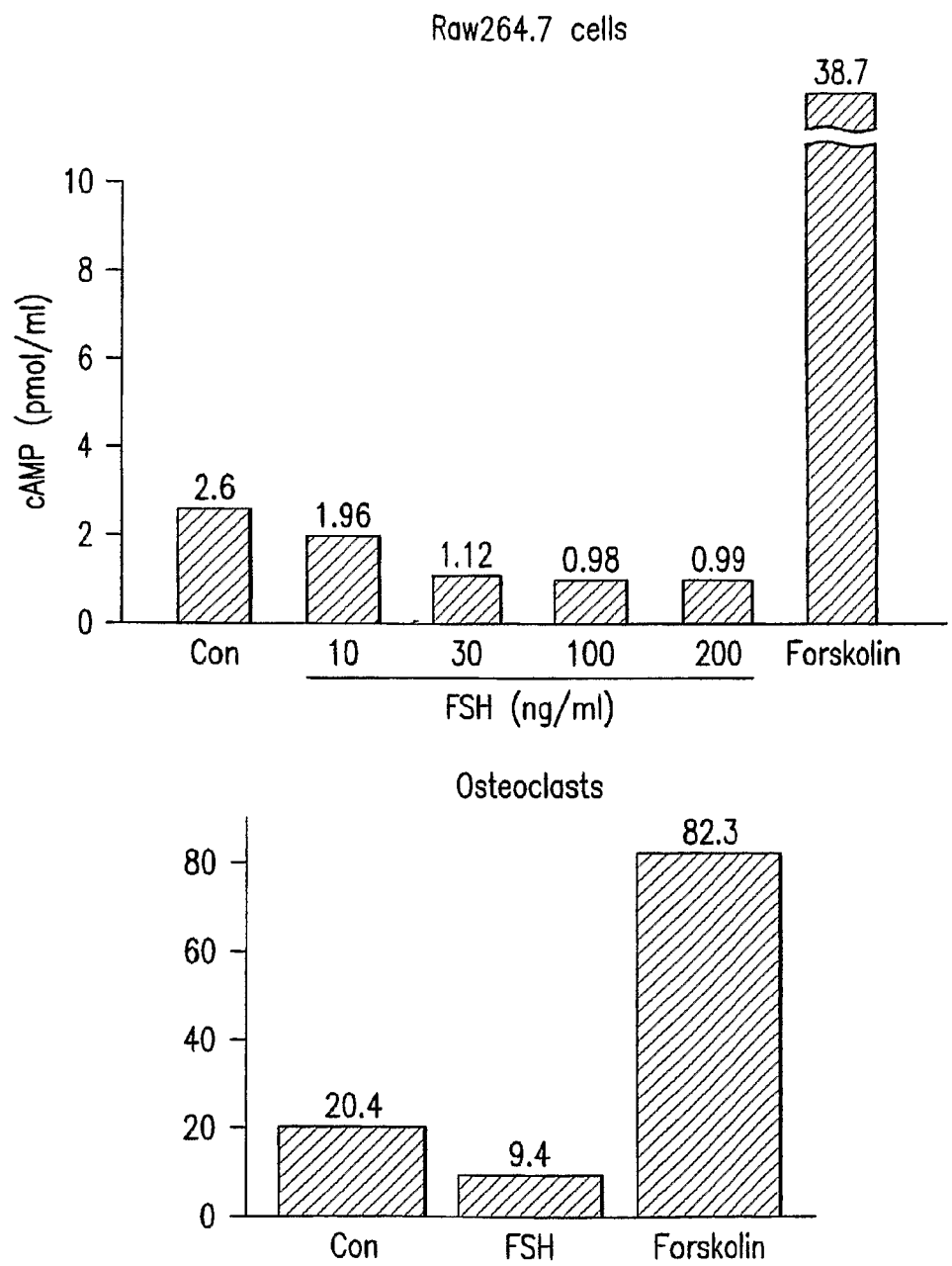
FIG. 7 shows that FSH reduced cAMP levels in osteoclasts and osteoclast precursor RAW cells.
Figure 8:
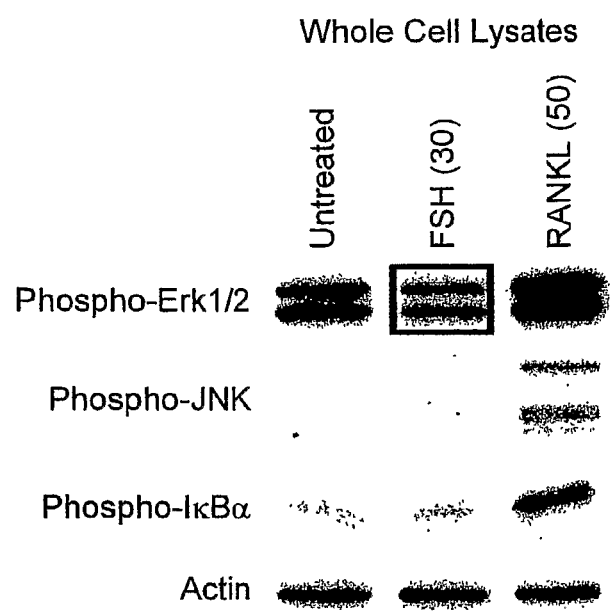
FIG. 8 shows that the phosphorylation of the MAP kinase, Erk1/2, was reduced with FSH, while JNK and IkBa phosphorylation were not.

This increase in osteoclast formation could result from increased proliferation or differentiation (maturation) of committed osteoclast precursors, or from an increased survival of cells that have already formed. To differentiate between these possibilities, we examined whether genes known to be up-regulated during osteoclast formation, namely TRAP, $\alpha 3$ integrin, vascular endothelial growth factor-c (VEGF-c) and cathepsin K, were also up-regulated with FSH. FIG. 5 shows results from real time PCR using specific primers to quantitate (measure) the specific cDNA species. Primer sequences are not shown, but will be available on request. The aforementioned osteoclast-specific differentiation genes were strongly up-regulated mostly in a concentration-dependent manner with FSH. Note that there was a significant drop in cathepsin K and $\alpha 3$ expression at higher FSH concentrations (100 and 300 ng/ml); the reason for this is unclear.

To examine this further, we examined the proliferation of osteoclast precursor RAW264.7 cells. FIG. 4b shows that various concentrations of FSH failed to affect cell proliferation. Together, the findings suggest that the effect of FSH on osteoclast formation mainly resulted from increased differentiation.

We also measured apoptosis by carrying out annexin V and propidium iodide staining. Apoptosis was reduced, notably cells that were positive for both dyes (late apoptosis) and annexin V alone (early apoptosis were inhibited with FSH. By prolonging survival FSH could increase the absolute number of osteoclasts in bone, and hence, increase overall bone loss.

cAMP signals are associated with reduced osteoclast formation and resorption, such as those generated by calcitonin. That cAMP levels are reduced could be a mechanism for enhanced osteoclast formation and/or resorption. The exact significance of reduction in Erk is under investigation.

We next tested the hypothesis that estrogen inhibits the expression of the FSH receptor in osteoclast precursors. For this, we obtained the FSH receptor promoter, which is the region of the FSH receptor gene that regulates its transcription. One of the ways to examine for transcriptional activity is to attach the promoter sequence to a firefly (luciferase) gene in a bacterial plasmid. This plasmid will glow when gene transcription is activated and vice versa. We also proposed to determine which regions of the promoter might be responsible for any effect of estrogen, and so, we made several deletion mutations that we similarly fused to luciferase gene.

First, the full length FSH receptor promoter (1548 bp long) was cloned into the pBL-luciferase plasmid to yield pBL-1548. Two further plasmids were created: one between 99 and 555 bp and another in the reverse direction to serve as negative control (DNA in the opposite direction is not the same as that in the normal direction). The plasmids were transfected into RAW-C3 cells that are known to possess estrogen receptors. The transfected cells were then exposed to 10-8M estrogen (and 30 ng/ml FSH for other experiments).

Figure 17:
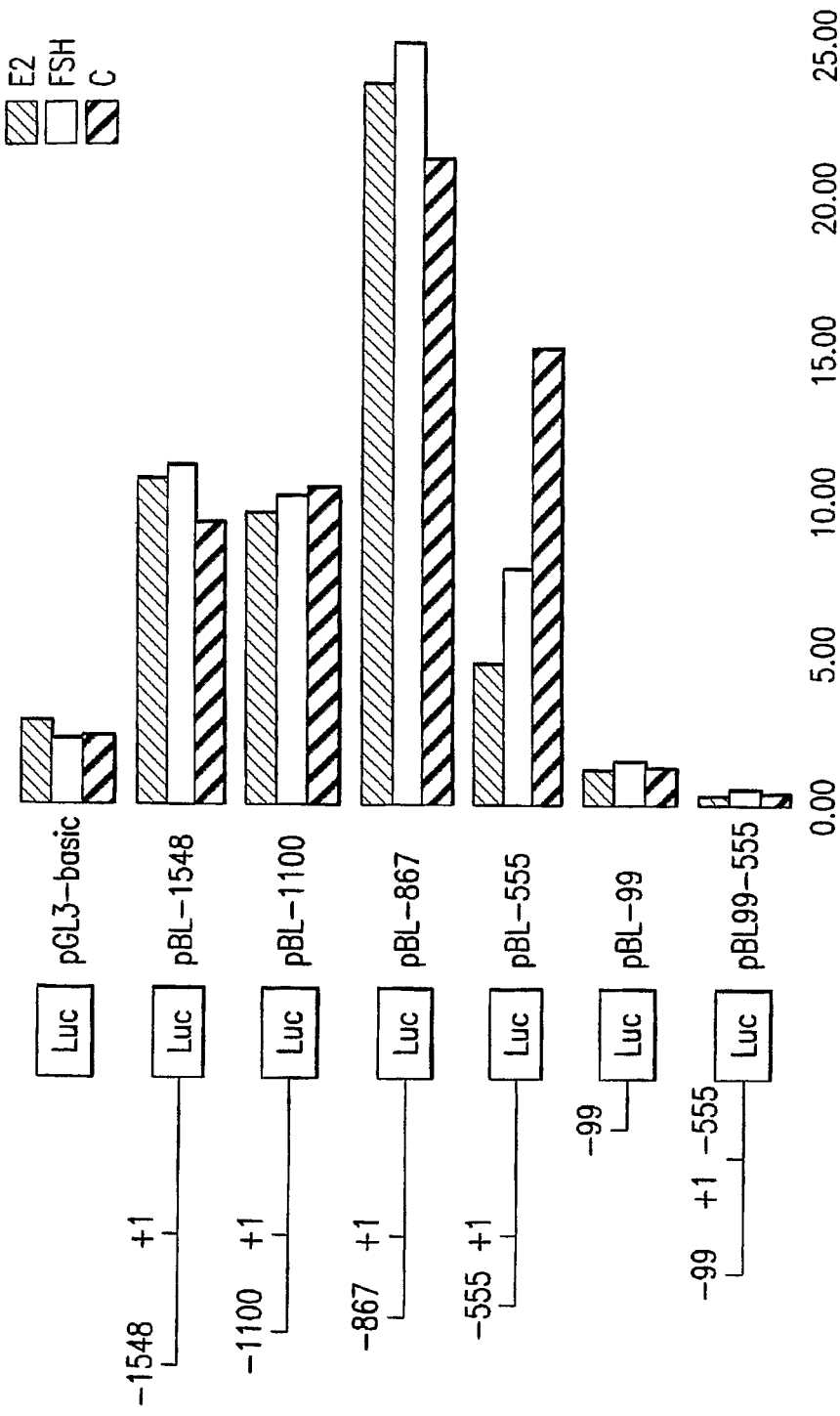
FIG. 17 depicts the results of FSHR promoter studies.

FIG. 17 shows the results of luminescence measurements in relative units. Three points need to be made. First, the first plasmid not containing the FSH receptor promoter, pGL3-basic, failed to produce luminescence. Second, all fragments of the produced luminescence except for the 99 bp fragment and the reverse pBL-99-555 fragment (negative controls). The latter confirmed specificity of the pBL-555-99 fragment; it lost activity when the DNA sequence was reversed. Finally, both estrogen and FSH suppressed FSH receptor expression.

One of the ways to study the importance of a given molecule vis-à-vis the skeleton is to delete the gene for that molecule and examine the effects of this maneuver on the skeleton. This strategy has been used extensively in bone biology (Karsenty, 2003).

Our laboratory has chosen to study mice lacking the FSHβ gene provided by Dr. T. Rajendra Kumar (now at the University of Kansas) (Kumar et al., 1997). Although the α subunit in these mice is intact, they do not have functional dimer and hence, have no active circulating FSH (Kumar et al, 1997). The heterozygotic mice (i.e. mice having the gene missing on one allele) have normal circulating estrogen levels and are fully fertile. As would be expected, mice lacking the FSHβ gene on both alleles—the homozygotes—are estrogen-deficient and sterile (Kumar et al, 1997).

Figure 16:
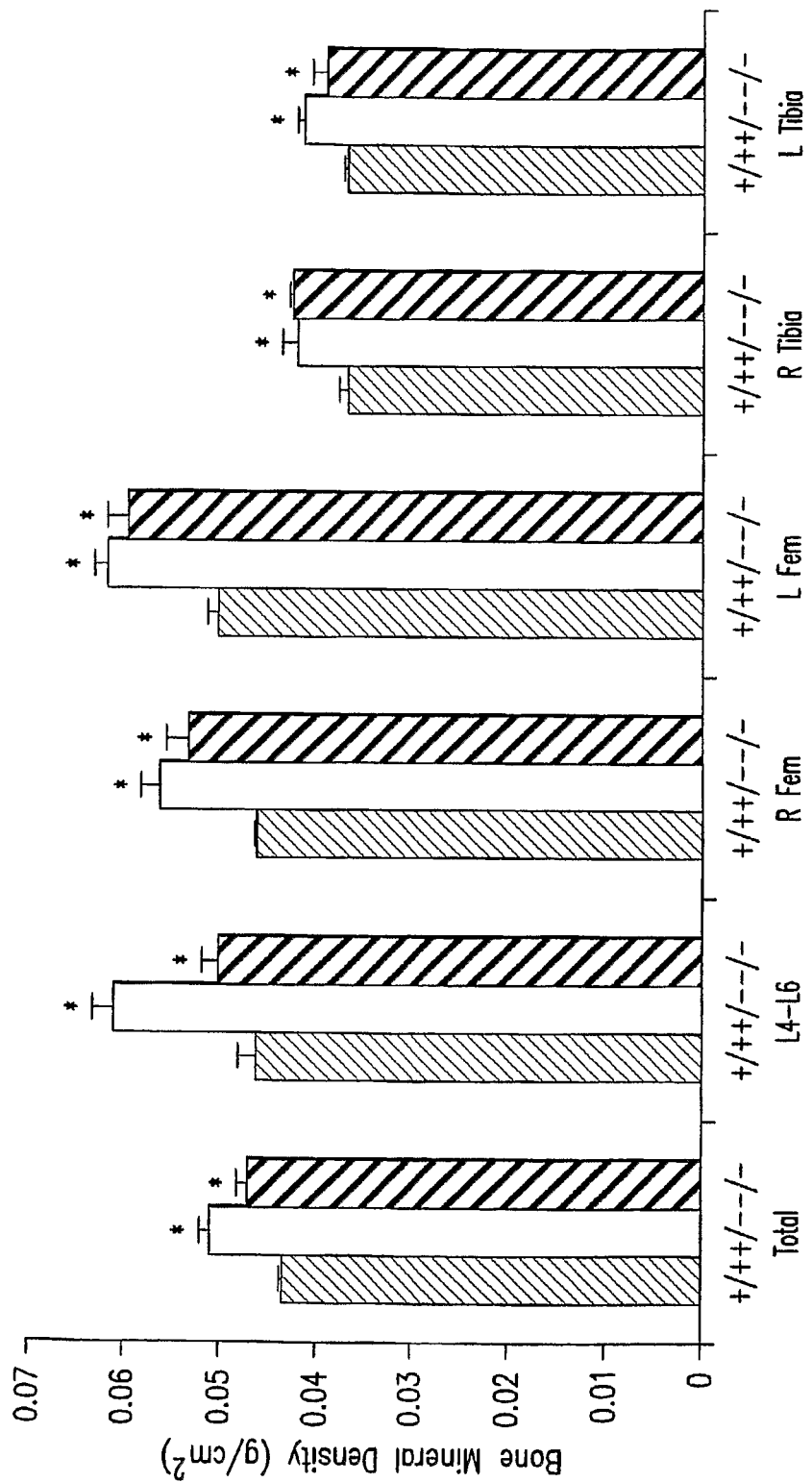
FIG. 16 shows Bone mineral density (BMD, cm2) in FSH knock out and heterozygote mice at various sites, as indicated. Note that the heterozygote mice, that are known to have normal estrogen levels, have an elevated BMD, indicating the effect of a 50% of circulating FSH on bone (low FSH levels would be expected to prevent bone loss).

FIG. 16 shows preliminary data relating to studies that have been obtained. These studies are critical as they provide in vivo genetic proof for the hypothesis that we had initially put forward based on our in vitro data—that FSH might stimulate bone loss. Changes in bone mineral density (BMD) at various sites, namely whole body, lumbar spine (mainly trabecular bone), femora, and tibiae (mainly cortical bone) were examined in FSHRβ knock out mice using Piximus, a small animal densitometer.

The hypothesis was that if FSH had a predominant effect on the skeleton, reduced FSH levels would protect against bone loss. That is, BMD would be greater in FSHβ+/−mice that have normal estrogen levels compared with control mice. FIG. 16 shows that this was indeed the case at all sites: FSHβ+/−mice (green bars) showed a significant (p<0.05) increase in BMD compared with wild type controls (pink bars) at all sites. The BMD also fell at most sites in the FSHβ−/−mice (yellow bars), likely due to estrogen deficiency. The greatest effect of partial FSHβ deletion was at the lumbar spine, the most reactive type of bone, whereas the mainly cortical bone in the tibiae showed the least effect. Overall, the results showing enhanced osteoclast formation in vitro appear to be consistent with the laboratory's in vivo findings showing a conservation of BMD in FSHβ deficient mice.

METHODS

Cell Culture, Osteoclast Formation Assay, and Immunostaining

Murine bone marrow cells were spun at 2000 rpm for 5 minutes at room temperature. The supernatant was removed carefully and completely. 10 ml fresh α-MEM with 10% FBS (fetal bovine serum) was added and the cells were re-suspended. The cells were then counted. Cells were then cultured to allow precursor proliferation in a 5 cm dish with 5 ml of α-MEM containing 10% FBS, M-CSF (macrophage colony stimulating factor) (5 ng/ml) and 1% P/S at 37° C. in 5% CO2 for 2 days. Non-adherent hematopoetic stem cell precursors were harvested and spun at 2000 rpm for 5 minutes. 10 ml of α-MEM and 10% FBS were added to the cell pellet that was re-suspended and mixed with 5 ml Ficoll-Paque Plus. The cell layer above the Ficoll was carefully isolated and spun at 200 rpm fox 15 minutes at room temperature. These purified precursors were washed once with α-MEM and 10% FBS, and then spun at 2000 rpm for 5 minutes at room temperature to remove the Ficoll. 1 ml of α-MEM plus 10% FBS were added and the cells were counted. The cells were finally seeded at densities of 5*10⁴/well and 1.5*10⁵/well in 96 well plates with α-MEM containing FBS (10%), MCSF (30 ng/ml), and RANK-L (60 ng/ml). The medium was changed every 3 days. The culture was stopped in 4-6 days depending on the level of cell differentiation.

RAW264.7 and RAW-C3 cells were similarly cultured for between 4 and 6 days in α-MEM containing 10% FBS and RANK-L (60 ng/ml), but without M-CSF (as these cells produce MCSF). A Sigma Kit and the manufacturer's protocol contained therein was followed in order to stain the cells for tartrate-resistant acid phosphatase (TRAP), an enzyme that characterizes mature osteoclasts. Cells positive for TRAP were then counted.

For immunostaining, osteoclasts, at day 1 and 4 of culture, were fixed with formaldehyde (10%), washed with phosphate buffered saline (PBS), and incubated with a polyclonal antibody to the human FSH receptor (1:100) or non-immune goat serum for 3 hrs (control). This followed by washing in PBS and further incubation in a second antibody (anti-goat IgG) labeled with fluorescein. Following several further washes, the cells were visualized under a confocal microscope (Zeiss) for surface staining.

Reverse Transcriptase Polymerase Chain Reaction (RT-PCR)

Total RNA was extracted and purified from osteoclast cultures using RNeasy Mini kit (Qiagen) per manufacturer's protocol. Appropriate primers that would yield a 200 bp FSH receptor product were designed.

5.0 µg total RNA was converted into cDNA using by Superscript II and 1/200 (~500 pg) was utilized for 40-cycle two-step PCR in the presence of 200 nM each of the forward and backward primers (Applied Biosystems, Foster City, Calif.). Amplicon size and reaction specificity was confirmed by agarose gel electrophoresis. Each transcript in each sample was assayed 3 times. The PCR product was sequenced commercially and its DNA sequence compared with the published DNA sequence from GeneBank.

Real Time Polymerase Chain Reaction

Unlike conventional PCR, real time PCR is utilized to quantitate RNA in a sample. 5 µg total RNA was first reverse transcribed (RT) into cDNA. 1/200 (approximately 500 pg) RT mixture was utilized for 40 cycle three-step PCR in an ABI Prism 7900HT (Applied Biosystems, Foster City, Calif.) in 20 mM Tris pH 8.4, 50 mM KCl, 5 mM MgCl2, 200 µM dNTPs, 0.5×SYBR Green I (Molecular Probes, Eugene, Oreg.), 200 nM each primer and 0.5 U Platinum Taq DNA polymerase (Invitrogen).

The cumulative fluorescence for each amplicon was normalized to that seen with GAPDH amplification. The target signal was plotted against the number of PCR cycles, and comparisons between samples made at the point where all the sample reactions were in the linear phase of amplification (the crossing threshold). The intersection of each amplification curve with the threshold yielded a CT (threshold cycle) value that reflected the relative amount of the original mRNA and cDNA. The more the initial transcript, the lower the CT value. The chosen primers were designed to yield close to 100% amplification efficiency; thus, each amplification cycle led to a doubling of amplified fragment. A CT of 20 represented twice as much starting mRNA as a CT of 21. The initial normalized value in each sample was represented by the ΔCT (target CT−GAPDH CT). The results were then calculated as the difference between each normalized reporter signal in a treated sample versus that in control tubes, yielding the ΔΔCT (treatment ΔCT−control ΔCT). Results were expressed as the fold-increase, at each time point, over the respective GAPDH controls (calculated as 2ΔΔCT). Means (+SEMs) were calculated from pooled data from up to three separate experiments, each with triplicate replicates.

The method was validated by demonstrating a single band of the expected size for each PCR amplicon by agarose gel electrophoresis. Primer quality was checked routinely by obtaining single sharp peaks upon melting point association analysis. These tests established the specificity of each PCR reaction, enabling accurate mRNA quantitation.

Construction of Mouse FSH Receptor Promoter-Luciferase Reporter Plasmids

The pBL-basic plasmid, which contains a multiple cloning site in front of the luciferase reporter gene, was used to produce a construct with the mouse FSH receptor promoter in front of a luciferase reporter gene. For this, a 1548 bp BamI/XhoI DNA fragment containing a FSHR promoter was ligated into BamHI/XhoI-cut pBL-Luciferase vector in front of the luciferase reporter gene-coding sequence to obtain the plasmid, pBL-1548. A number of deletion mutants were prepared using the endonuclease restriction sites of the promoter region present in pBL-1548. The pBL-1110 and pBL-867 mutants were constructed by digestion with PstI and HindIII, respectively. Using BamHI and BglII, we obtained two fragments, -1548/-555 ND-555/-99, which were used to construct, pBL-99, pBL-555-99 and pBL-99-555. The identities of all FSHR promoter constructs were verified by restriction mapping and commercial DNA sequencing. *E. coli* DH5α cells were the hosts for each plasmid. We then used QIAprep Spin Minprep Kit (Qiagen, Santa Clarita, Calif.) to purify the plasmid from the bacteria per manufacturer's instructions.

Transient Transfections

RAW-C3 cells were grown in MEM medium supplemented with 10% heat-inactivated (56° C. for 30 min) FBS (10%). The transfection protocol was chosen in order to keep ideal conditions for TransIT-Neural transfection reagent (Mirus). The cells were seeded in a 24-well plate at a density of 1.5×10⁵ cells/well and incubated at 37° C. in a humidified atmosphere of 5% CO₂/air overnight. TransIT-Neural transfection reagent-DNA complex was prepared by mixing 1 ml TransIT-Neural transfection reagent with promoter DNA (0.5 mg/well) and PKL-TK DNA (10 ng/well) in 50 ml Opti-MEM I medium without FBS. The mixture was incubated for 10 min at room temperature and then was carefully (drop by drop) added to the cells. The cells were incubated for 36 hours at 37° C./5% CO₂ and used for luciferase assays (see below).

Luciferase Assays

The cells were washed twice with PBS without calcium and magnesium. They were then covered with 0.1 ml of Reporter Lysis Buffer (Promega) per well and were cultured for 15 min on a king rocking platform at room temperature. The cells were transferred to the cell lysate using a microcentrifuge tube and stored at −70° C. Before making measurements, the tubes were centrifuged at maximum speed for 30 secs to clear the samples. The respective supernatants were transferred to fresh tubes at 0° C. and aliquots were assayed for luciferase activity using a chemiluminescent substrate. A 10 ml aliquot of clear extract was mixed with 50 ml of luciferase assay reagent (LARII) in the 96-well special multi-well plate. The plate was the placed in a luminometer (Top-Count NXT Microplate Scintillation Luminescence Counter, Packard Meriden, Conn.)). The first measurement was for firefly luciferase. Then, 50 ml of stop/Glo reagent was added to measure *Renilla luciferase* (for standardization).

BMD measurements were made on anesthetized animals using a small animal densitometer (Piximus) with a CV<1%.

Cell Culture, Immunoprecipitation, and Immunoblotting

The RAW264.7 monocyte/macrophage cell line was maintained in −MEM, 10% FBS, 100 U/ml penicillin, and 100

μg/ml streptomycin, at 37° C. in a humidified atmosphere. RAW264.7 cells were subcultured into 10 cm dishes at $1\times10^6$ per dish, and incubated for 24 hrs. The cells were then cultured in media with 1% FBS overnight, processed for various treatments, and lysed in 1% IGEPAL CA-630 (NP40), 150 mM NaCl, 50 mM Tris, 5 mM EDTA, 20 mM sodium fluoride (NaF), 1 mM sodium vanadate (NaV), 1 mM phenylmethylsulfonyl fluoride, 5 mM iodoacetamide, 10 μg/ml aprotinin (pH 8.0). The lysates were incubated with the polyclonal antibody of FSH receptor (ZYMED, San Francisco, Calif.) or normal rabbit serum, at 4° C. for 2 h followed by another 1 h incubation with protein G-Sepharose beads. The immunoprecipitates were washed three times with PBS containing inhibitors described above. Total cell lysates or immunoprecipitates were eluted from the beads by boiling in Laemmli sample buffer and separated by 8% SDS-PAGE. Proteins were transferred to PVDF membranes, immunoblotted with antibody of FSH receptor, and detected by ECL Western Blotting Detection Reagents (Amersham Biosciences).

Cyclic AMP Immunoassay

RAW264.7 cells were subcultured into 6 well culture plate at $5\times10^5$ per well, and incubated in –MEM, 10% FBS, for 48 hrs. For generation of osteoclasts, RAW264.7 cells were subcultured into 6 well culture plate at $1\times10^5$ per well, in the presence of RANKL 50 ng/ml. The media were changed at 48 hrs of incubation, and cells were incubated in the media with RANKL for another 48 hrs.

RAW264.7 cells or osteoclasts were incubated with 1 mM IBMX in –MEM media for 15 min, and processed for various treatments in the presence of IBMX for another 45 min. The content of cyclic AMP was measured by Cyclic AMP (low pH) Immunoassay kit (R&D Systems, Minneapolis, Minn.).
** Forskolin: 100 mM Detection of Apoptosis RAW264.7 cells were subcultured into 6 cm dishes at $5\times10^5$ per dish, and cultured for 48 hrs in a-MEM, 10% FBS. After culturing for 19 hrs in a-MEM without FBS, Annexin V binding was performed using a standard kit from BD Pharmingen (San Diego, Calif.) to measure apoptosis. Briefly, after rinsing cells twice with PBS, cells were suspended in 100 ml of 1× binding buffer, to which Annexin V-FITC (final: 5%, v/v) and propidium iodide (final: 2 mg/ml) were added. After a 15 min of incubation at room temperature, 400 ml of 1× binding buffer was added. Flow cytometry was performed using FACS Calibur ( ) and cells were analyzed with the Cellquest software.
** Annexin V(+) & PI(–): Early apoptotic cells
Annexin V(+) & PI(+): Late apoptotic cells and dead cells
** % increase: compared with cells cultured with normal serum, no serum starvation.

Flow Cytometric Analysis of FSH Receptor

Single cell suspensions of RAW264.7 cells treated with or without RANKL were stained with anti-FSH polyclonal antibody and FITC-conjugated bovine anti-rabbit antibody (Santa Cruz Biotechnology). Stained cells were analyzed with a FACS Calibur ( . . . ) using the Cellquest software.

In Vivo Determination of FSH Contribution to Osteoclast Development

Figure 9:
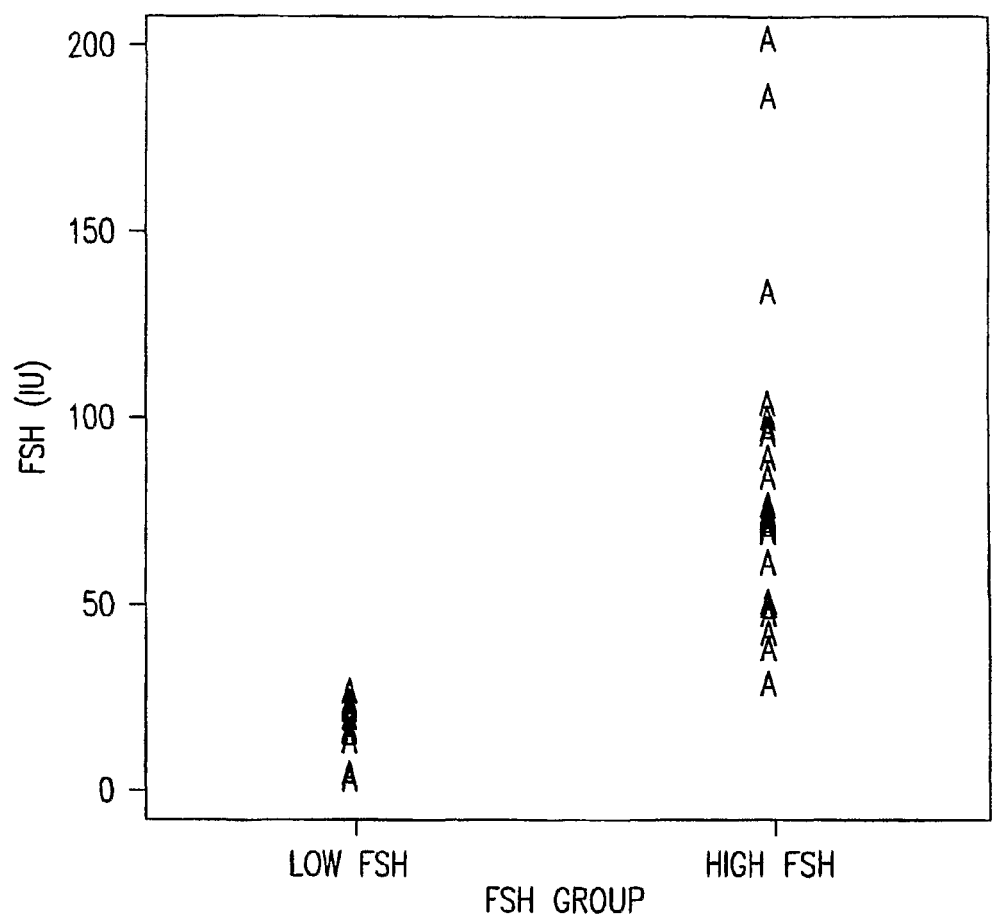
FIG. 9 shows distribution of FSH in postmenopausal women without and with estrogen replacement. Forty postmenopausal women ages sorted for FSH level using and elisa assay. The left group, with FSH<25 IU/ml, was estrogen replaced, the right group shows typical postmenopausal levels of FSH>25 IU/ml. The elisa assay was purchased from RDI, Flanders N.J. and was calibrated with duplicate blanks and standards from 0-100 IU/ml (FSH Elisa kit cat#RDI-1401KIT).

Forty serum samples from postmenopausal women 53-58 yrs, with last menstrual period>1 year prior to sampling, were collected from Magee-Womens Hospital, with IRB approval, and were stratified by FSH level into estrogen replaced and non-replaced subjects. The results of FSH serum concentrations for this population are shown in FIG. 9. In this age group, FSH is essentially always elevated in the absence of estrogen replacement.

Figure 10:
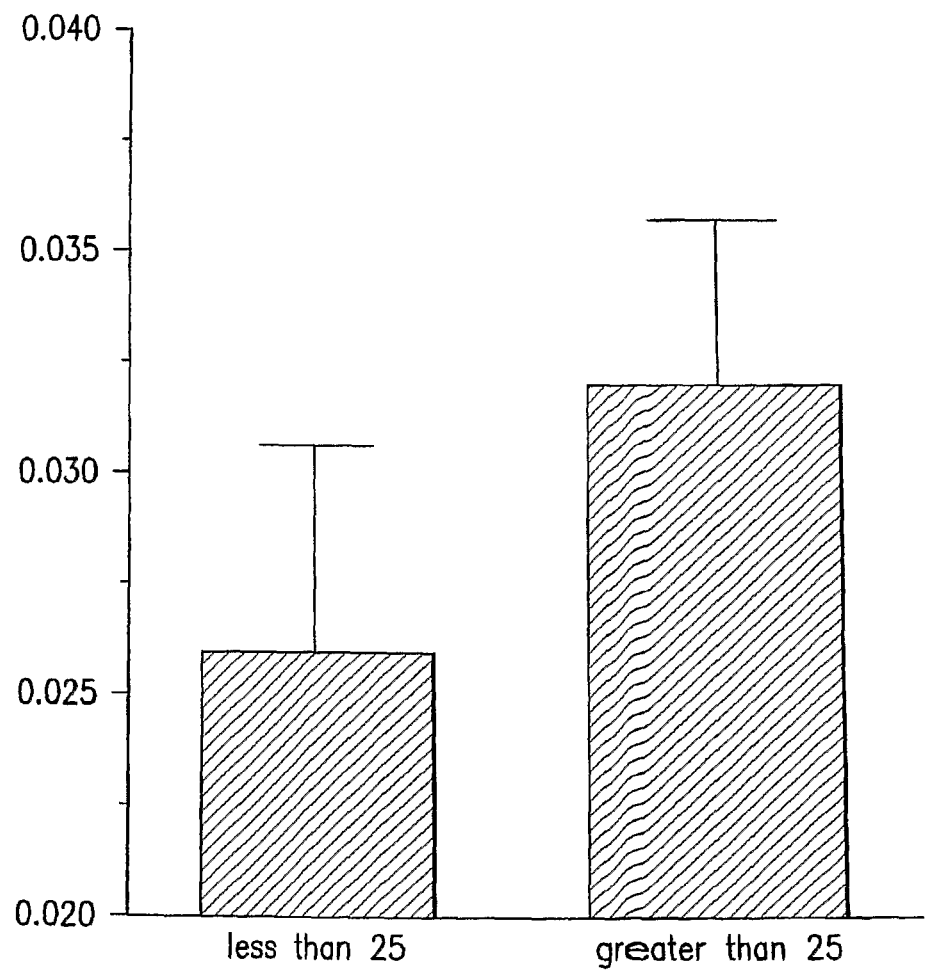
FIG. 10 shows difference in Lactate in low (left) and high (right) FSH groups. Lactate in mM from clinical multianalyzer. Mean±SD, n=12, 28 in low and high FSH groups. p<0.05.
Figure 11:
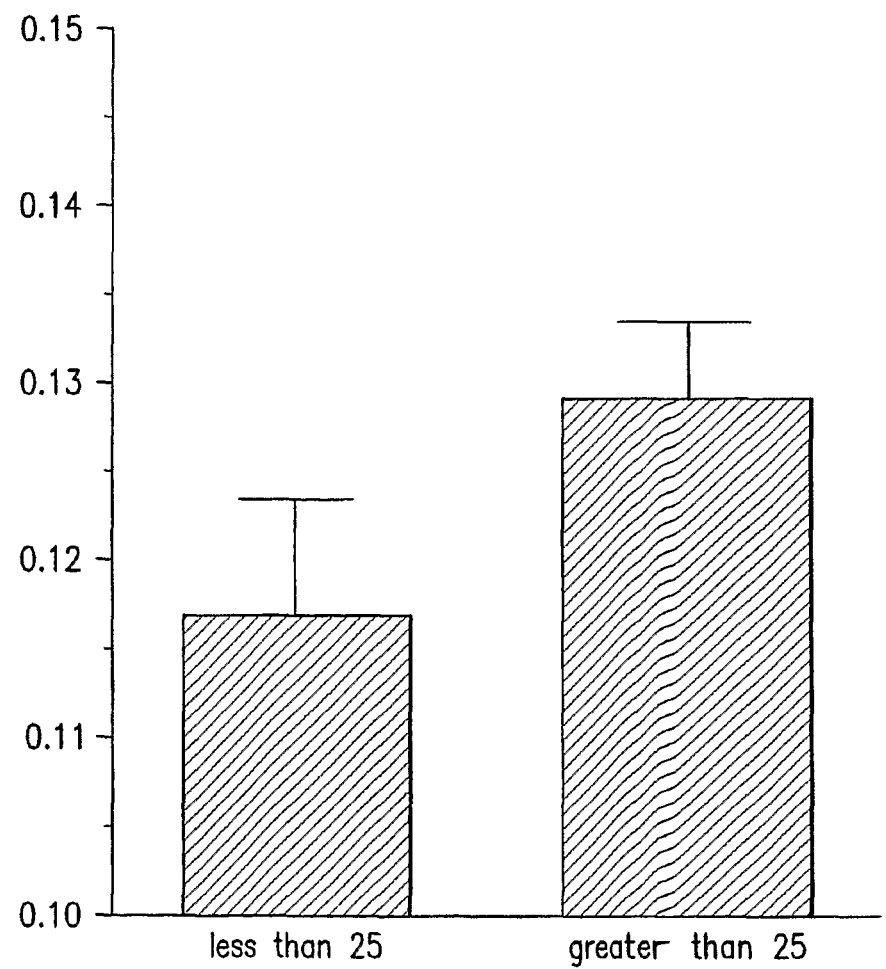
FIG. 11 shows difference in phosphate in low (left) and high (right) FSH groups. Phosphate in mM by clinical multi-analyzer. Mean±SEM, p<0.1.

Postmenopausal women are known to have a mild acidosis (anion gap), but its causes are not well characterized, and its response to estrogen was completely unknown. To characterize differences in acid-base balance, in each group, cations (Na, Ca, Mg, K) and anions ($PO_4$, $HCO_3$, Cl, lactic acid, and β-hydroxybutyrate) were measured using regular clinical laboratory instruments. Measurements failed to show differences in any analyte except lactic acid (lactate) and phosphate, where differences with $p<0.1$ were seen (FIGS. 10, 11).

Lactate and phosphate are known to increase with the menopause, but were not known to respond to estrogen replacement. Lactic acid is a metabolic product of anaerobic glycolysis and increases in anaerobic exercise or with certain metabolic stimuli. Phosphate, in the absence of other sources such as large dietary supplements, comes from the bone and reflects bone loss. Data from testicular macrophages suggests that lactate is directly driven by FSH. Thus, we queried whether bone osteoclasts respond directly to FSH, first by determining whether the receptor is present in human bone cells using unamplified gene screening (Table 1).

TABLE I

Gene screening findings in human bone cells.
Gene screen findings: FSH-R in human bone cells

| Cell type | Conclusion | P value, n = 16 |
|---|---|---|
| Human Osteoclasts and Macrophages | | |
| Osteoclasts From CD14 cells | Present | 0.02 |
| CD14 Osteoclast Precursors | Undetectible | 0.19 |
| Human MSCs, Fibroblasts, and Osteoblasts | | |
| Mesenchymal Stem Cells | Positive | 0.008 |
| Fibroblasts | Undetectible | 0.14 |
| Human Osteoblasts and MG63 cells | Undetectible | p > 0.1 (four determinations) |

Figure 12:
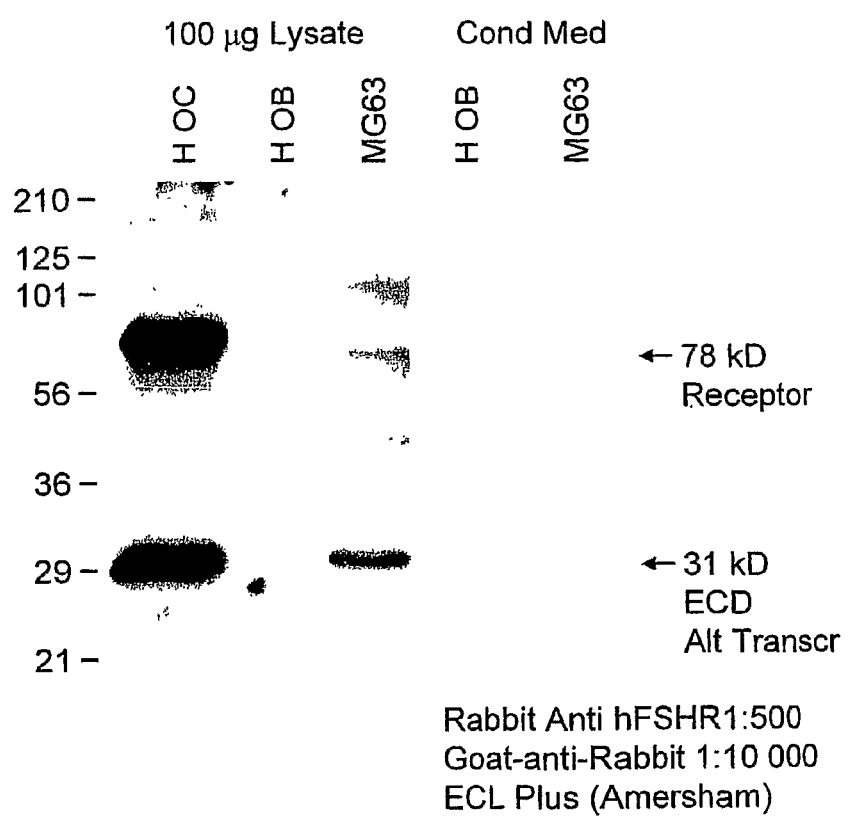
FIG. 12 shows Western blot for FSH-R in human osteoclasts and osteoblasts. Antibody was from Lifespan (Seattle, Wash.) and is a rabbit anti-human antibody to the N-terminal extracellular region, and is thus capable of detecting both full length (upper arrow) and truncated extracellular domain, probably a decoy receptor (lower arrow). Blot used 10 μg of protein or 10 μl of conditioned media (not concentrated), with primary antibody at 1:500, with primary binding detected by enhanced chemiluminescence.

To confirm the presence of FSH receptors, Western analysis was done (FIG. 12), using lysates of human osteoclasts and osteoblasts. This showed strong receptor expression in osteoclasts; expression in osteoblasts was very weak and possibly negative. We also examined conditioned media for the alternatively spliced extracellular only domain, which may function as a decoy receptor (lower arrow in FIG. 12). This was seen in osteoclast lysates, but not in conditioned media, although the media were not concentrated and the negative result may reflect excessive dilution of the analyte. The serum results in patients and presence of the receptor in human osteoclasts suggested that there is a physiological effect of FSH on human osteoclast differentiation or activity.

Figure 13:
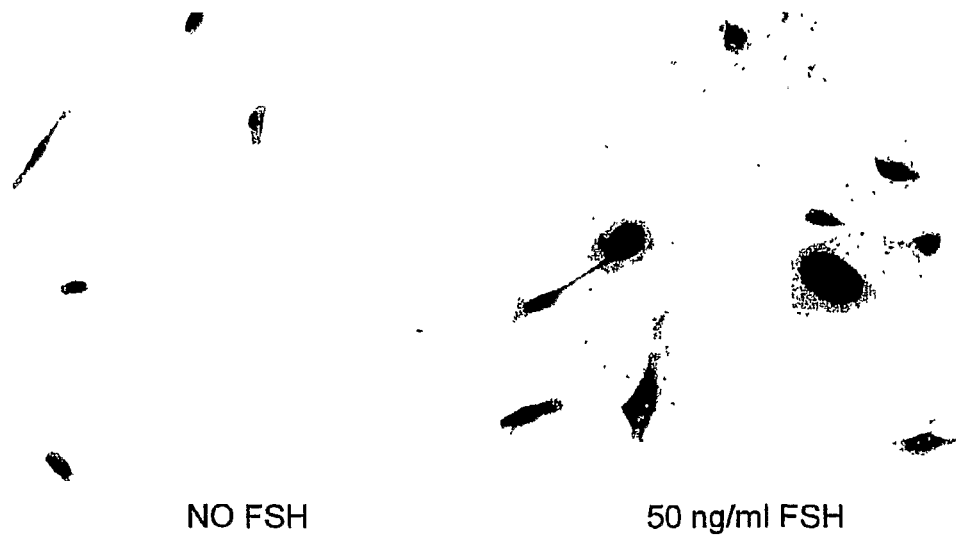
FIG. 13 shows human osteoclastic differentiation in vitro from CD24 cells is increased by FSH. The result shown tested cells at low density using standard osteoclast differentiation methods [3], and gave minimal differentiation in the absence of FSH and much stronger differentiation, with multinucleation, in the presence of 50 ng/ml FSH. This is representative of four assays, and gradations of effect were seen at lower (3, 10 ng/ml) FSH (not illustrated).

Experiments to test the hypothesis that the osteoclast is an FSH-responsive cell were then done. These included TRAP assays for osteoclast differentiation with and without FSH (FIG. 13). Osteoclast differentiation assays, from CD14 cells in 20 ng/ml RANKL and 10 ng/ml CSF-1, gave weak differentiation in control media; osteoclast formation is dependent on serum, cell density, and other factors and this result is not unexpected. However, there was a definite and consistent, increase in the amount of TRAP and multinucleation with addition of FSH, in keeping with the hypothesis of FSH response.

Figure 14:
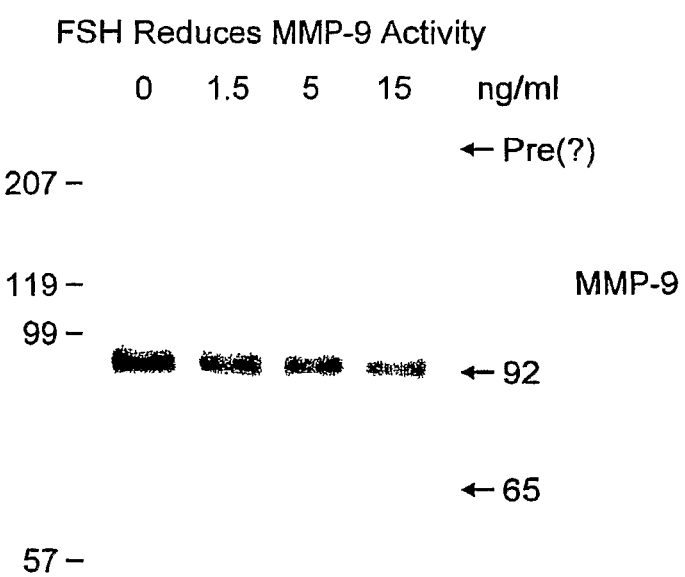
FIG. 14 shows the effect of FSH on MMP-9 activity in osteoclasts demonstrated by zymography. In cultures as in FIG. 10, with stated concentrations of FSH added, 7 d supernatants were collected and separated on 10% SDS-Page with 0.1% gelatin added. After running the gel, it was washed 1 h in 0.1% triton X-100 and then developed overnight in 10 mM phosphate buffer at pH 7.4 with 1 mM calcium added, and the degradation of collagen demonstrated by staining the gelatin with coomassie blue dye, photographing the gel, and making a negative image to show the degraded collagen as a positive image. High MW material is probably a precursor of the proteinase; recognized active forms at 65 and 92 kD are shown and 10 show the reduction of osteoclast formation and bone resorption in human osteoclasts.
Figure 15:
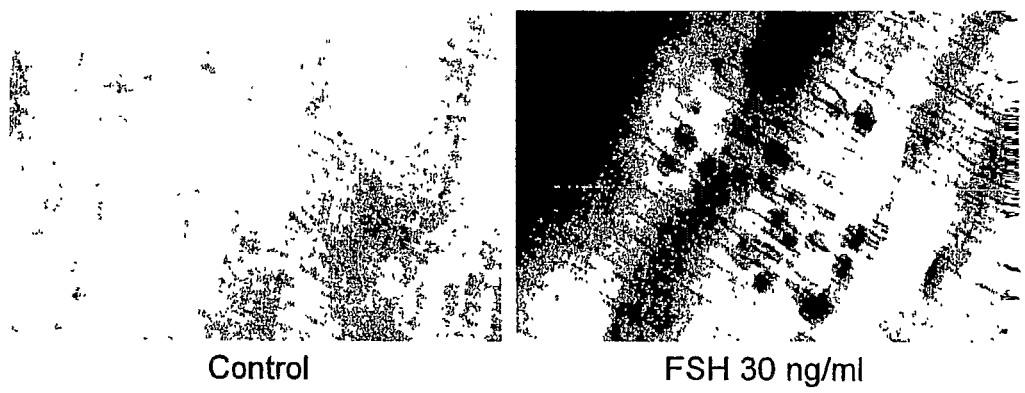
FIG. 15 shows the effect of FSH on activity of human osteoclast cultures demonstrated using dentine slices (pit assays). In the assay shown, made similarly to FIG. 10, cells were also plated on 5 mm round dentine slices for two weeks, which were then stained with toluidine blue. In quadruplicate assays, all control cells showed no pit complexes, while sporadic pit complexes were seen with FSH treatment (right). These are low power (20×) transmitted light photomicrographs of toluidine blue stained dentine; each field shown is 0.5 mm wide (blue-stained pits are ~40 μm across).

We also assayed MMP-9 activity in supernatants of these assays (FIG. 14). MMP-9 is a prominent osteoclast product, which is involved in extracellular matrix processing and also may be important in cytokine response. FSH caused a dramatic, dose dependent decline in supernatant MMP-9 activity. Further, pit assays were done (FIG. 15), using cells as in FIG. 5, but plated on 5 mm dentine chips. Pits were seen only at high FSH, and none at all in low FSH cultures.

We claim:

1. A method for inhibiting osteoclast differentiation in a cell population comprising at least one osteoclast or at least one osteoclast precursor cell, said method comprising providing an anti-follicle stimulating hormone (FSH) antibody or an anti-follicle stimulating hormone receptor (FSHR) antibody to said cell population, thereby inhibiting differentiation of said osteoclast or said osteoclast precursor cell.

2. The method of claim 1, wherein said cell population comprises said at least one osteoclast precursor cell.

3. The method of claim 1, wherein said cell population comprises said at least one osteoclast.

4. The method of claim 1, wherein said cell population is in vivo and comprises said at least one osteoclast, and wherein said anti-FSH antibody or said anti-FSHR antibody is provided to the vicinity of said at least one osteoclast in vivo.

5. A method for decreasing osteoclast-mediated bone resorption in a patient having a bone loss disorder caused by increased bone resorption, comprising administering a therapeutically effective amount of a composition comprising an anti-follicle stimulating hormone (FSH) antibody or an anti-follicle stimulating hormone receptor (FSHR) antibody to said patient.

6. The method of claim 5, wherein said bone loss disorder is selected from the group consisting of osteoporosis, Paget's disease, periodontitis, hypercalcemia, osteonecrosis, osteosarcoma, osteolyic metastases, familial expansile osteolysis, prosthetic loosening, periprostetic osteolysis, juxtaarticular bone destruction in rheumatoid arthritis and cleiodocranial dysplasia (CCD).

7. A method for decreasing osteoclast-mediated bone resorption in a patient having a bone loss disorder caused by increased bone resorption, the method comprising administering a composition comprising a therapeutically effective amount of an anti-follicle stimulating hormone (FSH) antibody to said patient.

8. The method of claim 7 wherein the antibody is a monoclonal antibody.

9. The method of claim 7 wherein the antibody is a humanized antibody.

10. The method of claim 7 wherein the antibody is a human antibody.

* * * * *

UNITED STATES PATENT AND TRADEMARK OFFICE
CERTIFICATE OF CORRECTION

PATENT NO. : 8,435,948 B2  Page 1 of 1
APPLICATION NO. : 11/664030
DATED : May 7, 2013
INVENTOR(S) : Zaidi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this
Eighth Day of September, 2015

Michelle K. Lee
*Director of the United States Patent and Trademark Office*